United States Patent
Mian et al.

(10) Patent No.: US 10,937,528 B2
(45) Date of Patent: Mar. 2, 2021

(54) CHRONIC DISEASE DISCOVERY AND MANAGEMENT SYSTEM

(71) Applicant: CURELATOR, INC., Palmer, MA (US)

(72) Inventors: Alec Mian, Palmer, MA (US); Marc Albert, Castellterçol Barcelona (ES); Francesc Peris, Barcelona (ES); Stephan Donoghue, North Yorkshire (GB)

(73) Assignee: Curelator, Inc., Palmer, MA (US)

( * ) Notice: Subject to any disclaimer, the term of this patent is extended or adjusted under 35 U.S.C. 154(b) by 954 days.

(21) Appl. No.: 15/502,087

(22) PCT Filed: Aug. 6, 2015

(86) PCT No.: PCT/US2015/043945
§ 371 (c)(1),
(2) Date: Feb. 6, 2017

(87) PCT Pub. No.: WO2016/022761
PCT Pub. Date: Feb. 11, 2016

(65) Prior Publication Data
US 2017/0235889 A1    Aug. 17, 2017

Related U.S. Application Data

(60) Provisional application No. 62/034,408, filed on Aug. 7, 2014, provisional application No. 62/120,534, filed
(Continued)

(51) Int. Cl.
*G16H 10/60*    (2018.01)
*G16H 15/00*    (2018.01)
(Continued)

(52) U.S. Cl.
CPC .......... *G16H 10/60* (2018.01); *A61B 5/02055* (2013.01); *A61B 5/4076* (2013.01);
(Continued)

(58) Field of Classification Search
CPC ........ G16H 50/20; G16H 50/30; G16H 20/00; G16H 10/20; G16H 10/60; G16H 15/00;
(Continued)

(56) References Cited

U.S. PATENT DOCUMENTS

| | | | |
|---|---|---|---|
| 5,937,387 A | * | 8/1999 | Summerell ......... G06F 19/3456 705/2 |
| 2002/0055857 A1 | | 5/2002 | Mault |

(Continued)

OTHER PUBLICATIONS

The International Search Report (ISR) with Written Opinion for PCT/US2015/043945 dated Oct. 28, 2015, pp. 1-12.
(Continued)

*Primary Examiner* — Joseph D Burgess
(74) *Attorney, Agent, or Firm* — McDonnell Boehnen Hulbert & Berghoff LLP

(57) ABSTRACT

The disclosed systems and methods include displaying disease trigger icons within a disease trigger map in a GUI, where the disease trigger map corresponds to a particular disease symptom, and where the position and size of a particular trigger icon within the trigger map based one or more of (i) the degree or strength of a statistical association between the trigger icon's corresponding disease trigger and the disease symptom, and (ii) a cumulative frequency and/or amount of exposure to the trigger icon's corresponding disease trigger. Some embodiments also include displaying a patient population disease trigger map one or more relationships between (i) one or more disease triggers and (ii) one or more patients of the patient population. Some embodiments may further include facilitating communica-
(Continued)

tion and/or disease trigger information sharing among patients.

26 Claims, 14 Drawing Sheets

Related U.S. Application Data on Feb. 25, 2015, provisional application No. 62/139,291, filed on Mar. 27, 2015, provisional application No. 62/148,130, filed on Apr. 15, 2015, provisional application No. 62/172,594, filed on Jun. 8, 2015.

(51) Int. Cl.
*G16H 50/20* (2018.01)
*A61B 5/00* (2006.01)
*G06Q 50/22* (2018.01)
*A61B 5/0205* (2006.01)
*A61B 5/024* (2006.01)
*A61B 5/11* (2006.01)
*A61B 5/145* (2006.01)

(52) U.S. Cl.
CPC .......... *A61B 5/6898* (2013.01); *A61B 5/7275* (2013.01); *A61B 5/742* (2013.01); *A61B 5/7435* (2013.01); *G06Q 50/22* (2013.01); *G16H 15/00* (2018.01); *G16H 50/20* (2018.01); *A61B 5/024* (2013.01); *A61B 5/0205* (2013.01); *A61B 5/1118* (2013.01); *A61B 5/14532* (2013.01); *A61B 5/4058* (2013.01); *A61B 2560/0242* (2013.01)

(58) Field of Classification Search
CPC ........ G16H 20/40; G16H 30/20; G16H 30/40; G16H 40/63; G16H 50/70; G16H 80/00; G16H 50/50; G16H 10/00; G06F 19/00; G06F 19/20; G06F 19/24; G06F 19/34; G06F 19/3418; G06F 19/3456; G06Q 50/22; G06Q 50/24

See application file for complete search history.

(56) References Cited

U.S. PATENT DOCUMENTS

| | | | |
|---|---|---|---|
| 2002/0184055 A1 | 12/2002 | Naghavi et al. | |
| 2005/0191678 A1 | 9/2005 | Lapointe et al. | |
| 2006/0272652 A1* | 12/2006 | Stocker | G16H 50/50 128/898 |
| 2008/0088629 A1* | 4/2008 | Lorenz | G16H 15/00 345/440.2 |
| 2009/0083070 A1* | 3/2009 | Giftakis | A61N 1/36135 705/2 |
| 2010/0323921 A1* | 12/2010 | Lau | C12Q 1/6886 506/16 |
| 2011/0184250 A1* | 7/2011 | Schmidt | G06Q 10/00 600/300 |
| 2013/0282395 A1* | 10/2013 | Rustgi | G06Q 10/06 705/2 |
| 2014/0142970 A1* | 5/2014 | Baronov | G06Q 50/22 705/2 |
| 2015/0356243 A1* | 12/2015 | Andreassen | G16B 20/00 702/20 |
| 2019/0387991 A1* | 12/2019 | Kuppuraj | A61B 5/04012 |

OTHER PUBLICATIONS

Stratton, Irene M. et al., "Association of glycaemia with macrovascular and microvascular complications of type 2 diabetes (UKPDS 35): prospective observational study" BMJ (2000) vol. 321, pp. 405-412.

* cited by examiner

CHRONIC DISEASE DISCOVERY AND MANAGEMENT SYSTEM

CROSS-REFERENCE TO RELATED APPLICATIONS

This application is a national stage of PCT application PCT/US15/43945, filed on Aug. 6, 2015. The PCT/US15/43945 application claims priority to U.S. provisional application 62/034,408 filed on Aug. 7, 2014; U.S. provisional application 62/120,534 filed on Feb. 25, 2015; U.S. provisional application 62/139,291 filed on Mar. 27, 2015; U.S. provisional application 62/148,130 filed on Apr. 15, 2015; and U.S. provisional application 62/172,594 filed on Jun. 8, 2015. The entire contents of the PCT/US15/43945; 62/034,408; 62/120,534; 62/139,291; 62/148,130; and 62/172,594 applications are incorporated herein by reference.

BACKGROUND

Some current techniques for patients to manage disease symptoms include keeping a written record of times when disease symptoms occur as well as times when the patient engages in potential triggering (and perhaps mitigating) activities. Other current techniques may include a patient keeping an electronic diary of disease symptoms, disease triggering/mitigating activities, along with perhaps other disease monitoring and management related data.

SUMMARY

Patients with chronic diseases may benefit from embodiments of the computer-based methods and systems described herein, which are configured to: (i) monitor and collect data about the patient's disease symptoms, disease factors, and/or disease triggers; (ii) aggregate and/or organize information regarding the patient's disease symptoms, disease factors, and/or disease triggers; (iii) determine statistical associations and/or correlations between (iii-a) the patient's disease symptoms and (iii-b) the patient's disease factors and/or disease triggers; (iv) identify the patient's disease factors and/or disease triggers that are most likely to cause the patient to experience a particular disease symptom and/or prevent the patient from experiencing a particular disease symptom; (v) inform the patient when they are at a high risk of experiencing a particular disease symptom; (vi) show the patient the impact that his or her conduct or environment might have on the patient's near term likelihood of experiencing the particular disease symptom; and/or (vii) generate and send messages (e.g., emails, text messages, or other types of messages or notifications) to and/or display such messages to a patient reminding the patient to (a) avoid engaging in certain activities that have been identified as increasing a likelihood of experiencing a disease symptom (i.e., disease triggers, as described herein), or (b) to engage in certain activities that have been identified as reducing the likelihood that the patient will experience the particular disease symptom (i.e., protectors, as described herein).

In some embodiments, one or more client devices operated by a patient, alone or in combination with external sensors and/or third-party information sources, are configured to monitor and collect data about the patient's disease symptoms, disease factors, and/or disease triggers. In operation, the client device(s) can be configured to: (i) send the collected disease symptom/factor/trigger data directly or indirectly to one or more servers for analysis; and/or (ii) arrange for collected disease symptom/factor/trigger data to be sent to the one or more servers for analysis. The one or more servers in turn, analyze the patient's disease symptom/factor/trigger input data, and send output data back to the patient's client device, which the patient's client device uses to perform a number of further steps, including but not limited to: (i) prompting the patient to input or otherwise provide additional disease symptom/factor/trigger input data; (ii) informing the patient when he or she is at a high risk of experiencing a particular disease symptom, which in some embodiments my include displaying a risk meter to the patient within a graphical user interface (GUI) on the patient's client device(s); and/or (iii) show the patient the impact that his or her conduct or environment might have on the patient's near term likelihood of experiencing the particular disease symptom, which in some embodiments may include displaying a disease trigger map within a GUI on the patient's client device(s).

As used herein, a disease symptom is a physical manifestation of a particular disease. In operation, a disease symptom can be characterized by multiple characterization metrics, including but not limited to one or more of: (i) a time (or range of times) when the patient experienced the disease symptom; (ii) a severity of the disease symptom; (iii) aspects or characteristics describing the disease symptom; and/or (iv) whether the disease symptom was accompanied by other related disease symptoms (and perhaps disease factors and/or disease triggers as well). In examples where the disease is migraine and the disease symptom is a migraine headache, the characterization metrics for the migraine headache symptom may include any one or more of: (i) when the headache occurred; (ii) how long the headache lasted; (iii) the intensity and/or severity of the headache; (iv) whether the headache was accompanied by other related symptoms such as nausea or dizziness, and if so, the time, duration, intensity/severity of the accompanying symptoms. Disease symptoms for other chronic diseases may include different characterization metrics.

As used herein, a disease factor is any event, exposure, action, or conduct related to and/or performed by a patient that has the potential to influence, affect, or cause the patient to experience a disease symptom, or in some cases, prevent the patient from experiencing a disease symptom. Disease factors may include both: (i) voluntary or modifiable conduct and/or experiences by the patient over which the patient has at least some control, such as consumption of a particular food product, ingestion of a particular therapeutic agent, application of a particular therapeutic agent, ingestion of a particular dietary supplement or drug, performance of a particular physical activity, and/or exposure to a particular chemical agent; and (ii) involuntary or un-modifiable conduct and/or experiences, such as exposure to environmental factors (e.g., smog, sunlight, rain, snow, high or low humidity, or high or low temperatures), ingestion or other exposure to mandatory therapeutic agents or drugs (e.g., drugs to maintain other diseases), and effects of other diseases or physical conditions over which the patient has little or perhaps effectively no control over.

Like a disease symptom, a disease factor can also be characterized by multiple characterization metrics, and different disease factors may have different characterization metrics. For example, for a food or drug consumption based disease factor, the characterization metrics may include, for example: (i) when the patient consumed the food or drug; and/or (ii) how much of the food or drug the patient consumed. Characterization metrics for an exposure based disease factor may include, for example: (i) when the patient was exposed; (ii) the intensity (e.g., bright sunlight) of the exposure; and/or (iii) the duration of the exposure.

In some embodiments, disease factors may also include premonitory symptoms or warning signs that may not actually cause the patient to experience a disease symptom, but may just be closely associated with onset of a disease symptom for a particular patient. To use the migraine example again, a premonitory symptom might be a craving for sweet foods perhaps caused by a chemical change in the patient's body before the patient experiences the migraine, but the sweet craving does not cause the migraine, but instead is likely caused by same chemical change that also causes the patient to experience the migraine.

In some instances, a particular physical manifestation felt by the patient may be a disease symptom or a disease factor depending on the context. To use the migraine example again, abnormal body temperature, abnormal heart rate, and abnormal blood sugar levels may be disease factors because they tend to cause a disease symptom such as migraine headache. But in other contexts, abnormal body temperature, abnormal heart rate, and abnormal blood sugar levels may be disease symptoms that are caused by other disease factors.

As used herein, a disease trigger is a disease factor that has been determined, for example through statistical analyses, to have a sufficiently strong association with a particular disease symptom for an individual patient. In some cases, a disease trigger may be strongly associated with causing the patient to experience the particular disease symptom, or at least increasing the risk or likelihood that the patient will experience the particular disease symptom. In other cases, a disease trigger may be strongly associated with preventing the patient from experiencing the particular disease symptom, or at least decreasing the risk or likelihood that the patient will experience the particular disease symptom; such disease triggers may be referred to herein as protectors because they tend to reduce the patient's likelihood of experiencing the disease symptom. In some embodiments, a disease trigger for a patient is a disease factor having a determined univariate association with a disease symptom for the patient, where the determined univariate association has a Cox Hazard Ratio greater than 1 and a p-value less than or equal to 0.05.

In some embodiments, one or more server systems analyze disease symptom and disease factor data received from a patient population to determine which disease factors rise to the level of disease triggers for a particular patient. In operation, a patient population may include many (hundreds, thousands, or perhaps millions) of patients who all share one or more similarities (e.g., the same age or age range, same gender, same ethnicity, same national origin, suffer from the same disease, have the same allergies, have the same genetic markers, and/or perhaps other similarities). Some patients may be members of multiple patient populations.

Some embodiments generally apply a two-step iterative approach to identify disease factors and triggers for a patient population, and then (based on the identified disease factors and triggers for the patient population) identify disease factors and triggers for an individual patient. For the first step, the server systems collect and analyze disease factor and disease trigger data from patients in a patient population to identify the disease factors that tend to be most strongly associated with a particular disease symptom for the patients in the patient population. Client devices (under direct or indirect control of the server systems) are configured to prompt patients in the patient population to enter characterization metrics for the disease factors that the server systems have determined to be most strongly associated with the particular disease symptom for the patient population. For the second step, the server systems analyze the disease factor characterization metrics for the patients in the patient population, and for each patient in the population, the server systems determine the strength of the association (for that patient) between particular disease factors and the disease symptom. Then, for each patient, the server systems designate the disease factors that are most strongly associated with the disease symptom as disease triggers for the patient. The process is iterative in that disease triggers identified for one patient in a patient population can be analyzed for the whole patient population and then tested for individual patients. Some aspects of this iterative, two-phase process are described in PCT Application PCT/US2014/013894 filed on Jan. 30, 2014, the contents of which are incorporated herein by reference.

Determination and/or designation of specific disease factors as disease triggers for a particular patient provides multiple advantages. For example, some embodiments may use a patient's determined disease triggers to prompt the patient to enter (or perhaps additionally or alternatively instruct sensors to collect) the most relevant disease data (i.e., the data about that patient's determined disease triggers).

Additionally, based on characterization metrics for the patient's disease triggers as reported by the patient and/or sensors (and the strength of the association(s) between the individual patient's experienced disease triggers and a disease symptom), some embodiments can predict when the individual patient is likely to experience a disease system, and inform the patient when he or she is at a high risk of experiencing a particular disease symptom. In some embodiments, informing the patient that he or she is at a high risk of experiencing a particular disease symptom may include displaying one or more aspects of the prediction in a "risk meter" within a GUI on the client device(s).

Also, based on the collected characterization metrics for the patient's disease triggers and the strength of the association(s) between the individual patient's experienced disease triggers and the disease symptom, some embodiments may additionally or alternatively show the patient the impact that his or her conduct or environment (as reflected in the collected characterization metrics for the patient's disease triggers) might have on the patient's near term likelihood of experiencing the particular disease symptom. In some embodiments, showing the patient the impact that his or her conduct or environment might have on the patient's near term likelihood of experiencing the particular disease symptom may include displaying a "trigger map" within a GUI on the client device(s).

In operation, the trigger map may include a plurality of "trigger icons" (or similar indications), where each trigger icon corresponds to at least one of the individual patient's determined disease triggers. The position and size of a particular trigger icon within a patient's trigger map in some embodiments may be based one or more of: (i) the degree or strength of the association between the trigger icon's corresponding disease trigger and the disease symptom for the patient (e.g., the Cox Hazard Ratio, logistic regression odds ratio, p-value, or other quantification of the association); (ii) a cumulative frequency of the patient's exposure to the disease trigger; and/or (iii) the amount of exposure and/or cumulative exposure.

Some embodiments may additionally or alternatively include displaying a patient population trigger map for a disease symptom within a GUI. In operation, the patient population trigger map shows relationships between (i) one or more disease triggers of one or more patients in a particular patient population and (ii) one or more patients of the patient population. In such embodiments, a patient and/or researcher may review and consider (i) how a particular patient's disease triggers compare with other patients in that particular patient's patient population, (ii) whether and the extent to which certain disease triggers may be more or less prevalent within a particular patient population, and/or (iii) whether and the extent to which a patient may have more or fewer disease triggers as compared to other patients in that patient's patient population. As mentioned previously, a patient population may include many (hundreds, thousands, or perhaps millions) of patients who all share one or more similarities (e.g., the same age or age range, same gender, same ethnicity, same national origin, suffer from the same disease, have the same allergies, have the same genetic markers, and/or perhaps other similarities). Some patients may be members of multiple patient populations.

In some embodiments, the patient population trigger map includes one or more input fields that enable trigger data to be sorted, filtered, and/or analyzed on one or more of a number of factors, including but not limited to patient, patient population, gender, age, age range, geographic location, ethnicity, national origin, type or location of employment, route of travel, medical treatment, genetic marker, disease symptom, disease symptom severity, disease symptom frequency, disease trigger, and disease protector. In operation, the sorted and/or filtered data is displayed in the patient population trigger map to help patients and/or researchers identify similarities in disease symptom manifestation and disease symptoms/protectors for patients in the patient population.

Some embodiments may further include electronic messaging capabilities that enable patients in the patient population to communicate with each other (preferably in an anonymized fashion, but not required) to share information and/or recommendations about personal experiences with their own disease symptoms and disease triggers/protectors, which in turn may prompt other patients to experiment with recommended triggers/protectors and document their experience with those triggers/protectors in the system, thereby providing the system with more disease trigger information for analysis and helping patients gain a better understanding of their own disease symptoms and triggers through the exchange and sharing of information.

Some embodiments may also further include a server system generating and sending messages to a patient reminding or encouraging the patient to (a) avoid engaging in certain activities that have been identified through statistical analysis as increasing that particular patient's likelihood of experiencing a disease symptom (i.e., that particular patient's disease triggers), or (b) to engage in certain activities that have been identified through statistical analysis as reducing that particular patient's likelihood of experiencing the particular disease symptom (i.e., that particular patient's protectors). In operation, such messages may include any one or more of emails, text messages, in-app messages, or other types of electronic messaging. In some embodiments, the system is configured to generate and send the above-described messages to patients on a daily or weekly basis, but the frequency of the messages could be more or less than daily or weekly. Additionally or alternatively, some embodiments may include sending the above-described messages in response to determining that the patient is at a heightened risk of experiencing a disease symptom, for example, in connection with the risk meter described herein. In operation, a patient's computing device receives and displays the messages within a GUI. Some embodiments may also include prompting the patient to enter trigger and/or protector information indicating whether and the extent to which the patient has complied with the recommendations in the message.

The systems and methods disclosed herein provide the above-described features and functionality and other benefits and capabilities. As a result, the disclosed systems and methods provide improvements to shortcomings of existing methods for chronic disease management within the healthcare field by using patient population level and individual patient level statistical analyses to identify the disease triggers that are most relevant to a specific patient's disease symptom, collecting the most relevant disease trigger data for a patient based on the patient's specific history (near and long term) of disease trigger exposure via the disclosed prompting mechanisms, and informing the patient how his or her actual exposure to his or her specific disease triggers and protectors increases or decreases his or her corresponding likelihood of experiencing the disease symptom in an easy to understand and intuitive fashion via the risk meter and trigger map features. By providing the patient with the above-described information and analysis results on his or her personal disease triggers and related disease information, embodiments of the disclosed systems and methods enable a patient who suffers from a chronic disease to alter his or her behavior and/or change his or her environment to reduce the risk of experiencing one or more disease symptoms, and in some instances, avoid experiencing a disease symptom altogether.

The foregoing summary is illustrative only and is not intended to be in any way limiting. In addition to the illustrative aspects, embodiments, and features described above, further aspects, embodiments, and features will become apparent by reference to the figures and the following detailed description.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, can be arranged, substituted, combined, separated, and designed in a wide variety of different configurations, all of which are explicitly contemplated herein.

Embodiments of the systems and methods disclosed herein generally include: (i) monitoring and collecting data about a patient's disease symptoms, disease factors, and/or disease triggers; (ii) aggregating and/or organizing information regarding the patient's disease symptoms, disease factors, and/or disease triggers; (iii) determining associations and/or correlations between (iii-a) the patient's disease symptom(s) and (iii-b) the patient's disease factors and/or disease triggers; (iv) identifying the patient's disease factors and/or disease triggers that are most likely to cause the patient to experience a particular disease symptom and/or prevent the patient from experiencing a particular disease symptom; (v) informing the patient when they are at a high risk of experiencing a particular disease symptom, such as with a risk meter; (vi) showing the patient the impact that his or her conduct or environment has had, may have had, or potentially could have on his or her near term likelihood of experiencing the particular disease symptom, such as with a trigger map and/or (vii) generating and sending messages (e.g., emails, text messages, or other types of messages) to a patient (a) discouraging the patient from engaging in certain activities identified through statistical analysis as increasing the patient's likelihood of experiencing a disease symptom, and/or (b) encouraging the patient to engage in certain activities identified through statistical analysis as reducing the patient's likelihood of experiencing the particular disease symptom. In some embodiments, in response to receiving such messages, a GUI on a patient's computing device displays the received message, and/or formats and displays the received message to the patient, perhaps with prompts encouraging the user to document whether he or she followed the recommended actions in the message.

System Overview

Figure 1:
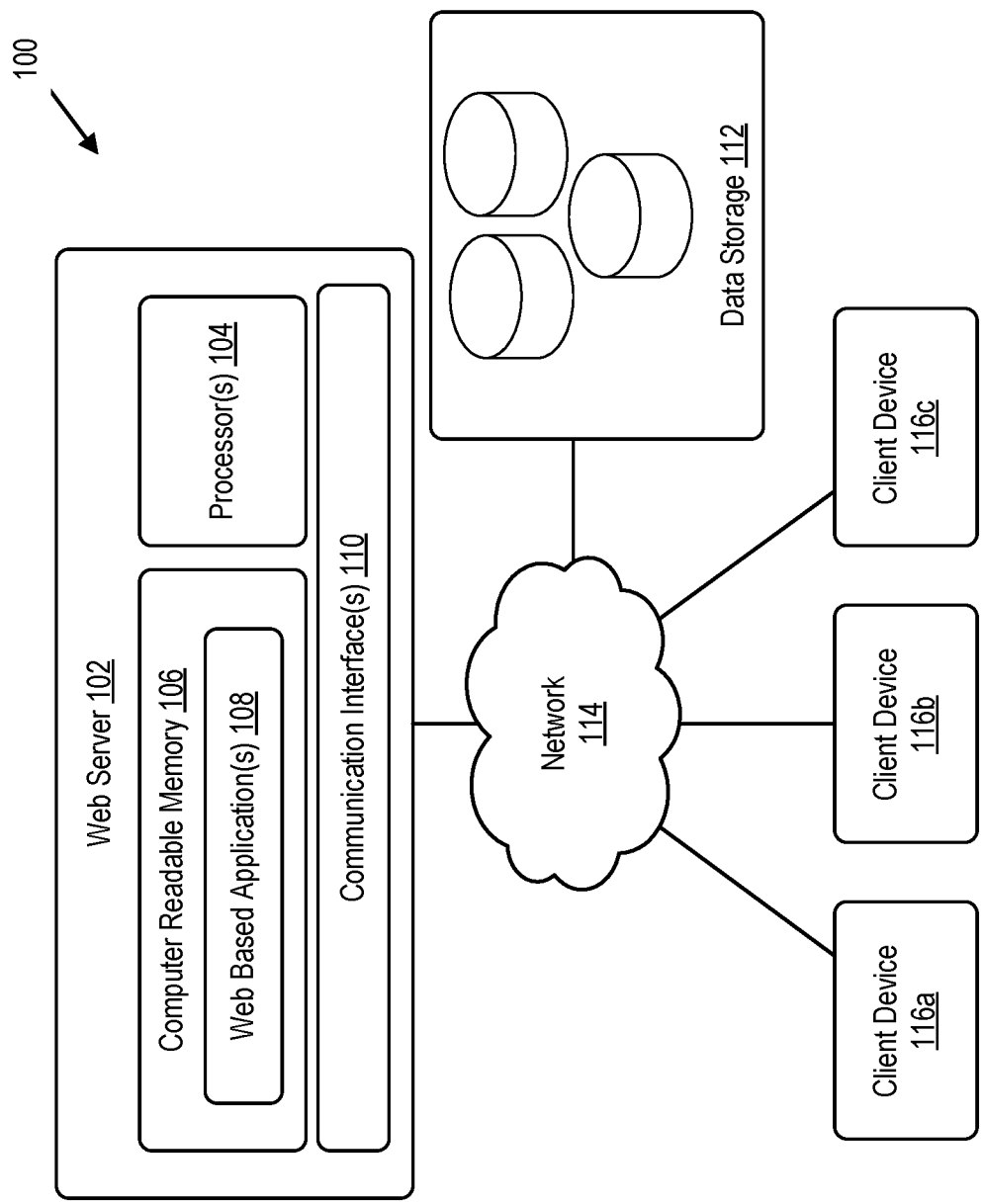
FIG. 1 shows an example web-based client-server computing system according to some embodiments.

FIG. 1 shows an example web-based client-server computing system 100 according to some embodiments. The example system 100 includes a web server 102 and data storage 112. In operation, the web server 102 is configured to communicate with a plurality of client devices 116a-b over a network 114. In operation, network 114 may comprise one or more of: (i) a local area network (LAN); (ii) a wide area network (WAN); and/or (iii) the Internet or other combination of wired and/or wireless communications networks.

The web server 102 includes one or more processors 104, computer readable memory 106, and one or more communication interfaces 110.

Each of the one or more processor 104 may be any type of processor now known or later developed, including but not limited to a general purpose processor, special purpose processor, application specific integrated circuitry (ASIC), or other type of processor configured to execute computer program instructions.

The computer readable memory 106 may be any type of tangible, non-transitory computer memory now known or later developed, including but not limited to magnetic memory, optical memory, hard discs, optical discs, flash memory, or other type of memory configured to store program code and/or other data. In operation, the computer readable memory 106 is configured to store at least one or more web based applications 108 (or other computing applications), that when executed by the one or more processors 104, cause the web server 102 to perform one or more computing and communications functions, such as the computing and communications functions described herein.

The one or more communication interfaces 110 may be any type of communication interface now known or later developed, including but not limited to wired, wireless, or optical communication interfaces configured to enable the web server 102 to access data storage 112 and to enable the web server to communicate and exchange information with the plurality of client devices 116a-b.

The data storage 112 may be any type of information storage medium, such as computer readable memory. In some embodiments, the data storage 112 is configured as a database system for storing disease symptom, disease factor, and disease trigger data for a plurality of patients and patient populations. In operation, the web server 102 writes data to and reads data from data storage 112 as part of performing the computing and communication functions described herein.

In operation, the web server 102 is configured to receive disease symptom, disease factor, and disease trigger data for individual patients and patient populations, and more particularly, characterization metrics that describe patients' disease symptoms, disease factors, and disease triggers. Characterization metrics for a patient's disease symptoms/factors/triggers may originate from one or more of a variety of sources, including but not limited to: (i) data that the patient manually enters into his or her client device via a GUI on the client device; (ii) data collected by sensors that are integrated with a patient's client device (e.g., a mobile phone or similar device), including but not limited to integrated optical sensors, cameras, location sensors, motion detectors, gyroscopes, accelerometers, and GPS transceivers; (iii) data collected by medical and/or biometric sensors, that are communicatively coupled to one or both of the patient's client device(s) and/or the web server 102, including but not limited to sensors that detect the patient's temperature, heart rate, blood sugar level, and/or physical activity, e.g., pedometers, thermometers, heart-rate monitors, glucose monitors, or similar sensors/motions; (iv) data collected by environmental sensors that are communicatively coupled to one or both of the patient's client device(s) and/or the web server 102, including but not limited to thermometers (to measure atmospheric temperature), barometers (to measure air pressure), microphones (to measure ambient sound), optical sensors (to measure light intensity and/or color); and/or (v) data collected from third-party information sources, such as news or weather information services, that are communicatively coupled to one or both of the patient's client device(s) and/or the web server 102, including but not limited to weather, pollen, and/or pollutant data, etc. from servers that provide environmental data related to an area where the patient is located or was located in the past.

The client device(s), biometric sensors, environmental sensors, and third party information sources (collectively, the disease symptom/factor/trigger data sources) may be configured or otherwise instructed to send collected disease symptom/factor/trigger data to the web server 102 in "real-time" (e.g., essentially as soon as the data is available to be sent to the web server 102). Alternatively, the disease symptom/factor/trigger data sources may collect the symptom/factor/trigger data over time, and then periodically send the symptom/factor/trigger data to the web server 102 in batches at regular or semi-regular intervals (every 15 minutes, half hour, hourly, etc.). In some embodiments, certain symptom/factor/trigger data may be identified as "high priority" symptom/factor/trigger data, and the disease symptom/factor/trigger data sources may be configured to send such "high priority" symptom/factor/trigger data to the web server 102 in an expedited fashion. For example, a client device may send "high priority" symptom/factor/trigger data to the web server 102 immediately (or substantially immediately) in response to receiving such symptom/factor/trigger data (or a very short time thereafter) rather than holding and sending such symptom/factor/trigger data to the web server 102 at a later time.

After receiving the symptom/factor/trigger data from any of the above-described disease symptom/factor/trigger data sources, the web server 102 analyzes the received symptom/factor/trigger data to determine one or more of: (i) associations and/or correlations between (i-a) disease symptoms and (i-b) disease factors and/or triggers; (ii) which disease factors are most strongly or highly associated with a particular disease system; and/or (iii) which disease factors are disease triggers for individual patients. Some embodiments generally apply a two-step iterative approach for analyzing the disease symptom/factor/trigger data. First, the web server 102 analyzes the received symptom/factor/trigger data from all of the patients in a patient population to identify the disease factors and/or triggers that tend to be most strongly associated with a particular disease symptom for the patients in the patient population. This process is described in more detail with reference to FIG. 7.

Next, the web server 102 analyzes an individual patient's disease symptom/factor/trigger data to one or more of: (i) identify, for that particular patient, which disease factors are most strongly associated with that patient's disease symptom(s); and/or (ii) identify, for that particular patient, which disease factors have a sufficiently strong association with the patient's disease symptom(s) to be identified as a disease trigger for that patient, including, for example, identifying the patient's disease factors/triggers that are most likely to cause the patient to experience a particular disease symptom and/or prevent the patient from experiencing a particular disease symptom. This process is described in more detail with reference to FIG. 8.

Because the potential universe of disease factors and triggers is so large, web server 102 can use the disease factors/triggers that are determined to be most strongly associated with a disease symptom for a patient population and/or a particular patient to help determine which actual and/or potential disease factors and disease triggers to focus on. In some embodiments, the web server 102 may instruct a patient's client device to prompt the patient to enter relevant disease symptom/factor/trigger data at particular times or in response to particular events, as described in more detail with regard to FIGS. 3-6.

In some embodiments, prompting the patient to enter specific disease symptom/factor/trigger data at specific times or in response to specific events improves the quality and quantity of relevant data collected from the patient. In operation, a higher quantity of higher quality disease symptom/factor/trigger data should improve the web server's 102 disease symptom/factor/trigger associations and disease trigger determinations for patient populations and individual patients. With better (e.g., more reliable and accurate) symptom/factor/trigger associations and disease trigger determinations for an individual patient, the web server 102 can: (i) provide the patient's client device(s) with information describing the likelihood that the patient will experience (or not experience) a particular disease symptom in the near future, which the patient's client device(s) may in turn use to display a "risk meter" within a GUI on the patient's client device(s), as described in more detail with regard to FIGS. 9 and 11; and/or (ii) provide the patient's client device(s) with information on symptom/factor/trigger associations and disease trigger determinations, which the patient's client device(s) may in turn use to show the patient the impact that his or her conduct or environment might have on his or her near term likelihood of experiencing the particular disease symptom, which in some embodiments may include displaying a disease "trigger map" within a GUI on the patient's client device(s), as shown and described with reference to FIGS. 10 and 11.

Each of the client computing devices 116a-b, sometimes referred to herein as client devices or simply clients, may be any of a smartphone, a tablet computer, a laptop computer, a desktop computer, or any other computing device now known or later developed. In operation, individual client devices 116a-c are configured to perform various functions, including but not limited to: (i) receiving, collecting, or otherwise obtaining disease symptom/factor/trigger data from patient inputs and/or sensor readings; (ii) sending disease symptom/factor/trigger data to the web server 102 and/or the data storage 112 (and/or perhaps arranging for disease symptom/factor/trigger data to be sent to the web server 102 and/or the data storage 112); (iii) receiving instructions for prompting patients to enter specific disease symptom/factor/trigger data, and in response, prompting patients to enter the specific disease symptom/factor/trigger data via GUI prompts; (iv) receiving information describing the likelihood that the patient will experience (or not experience) a particular disease symptom in the near future for use with displaying a "risk meter" to the patient, and displaying a "risk meter" within a GUI on the client device(s); and/or (v) receiving information on symptom/factor/trigger associations and disease trigger determinations for use with displaying a "trigger map" to the patient, and displaying the trigger map within a GUI on the client device(s).

Each client device 116a-c typically includes a user-interface, a processor, and/or computer-readable media storing program instructions executable by the processor for performing certain features or functionality described herein. The user-interface may include input devices such as one or more buttons, cameras, microphones, or touchscreens, as well as output devices such as a touchscreen, a display screen, and/or one or more speakers.

Figure 2:
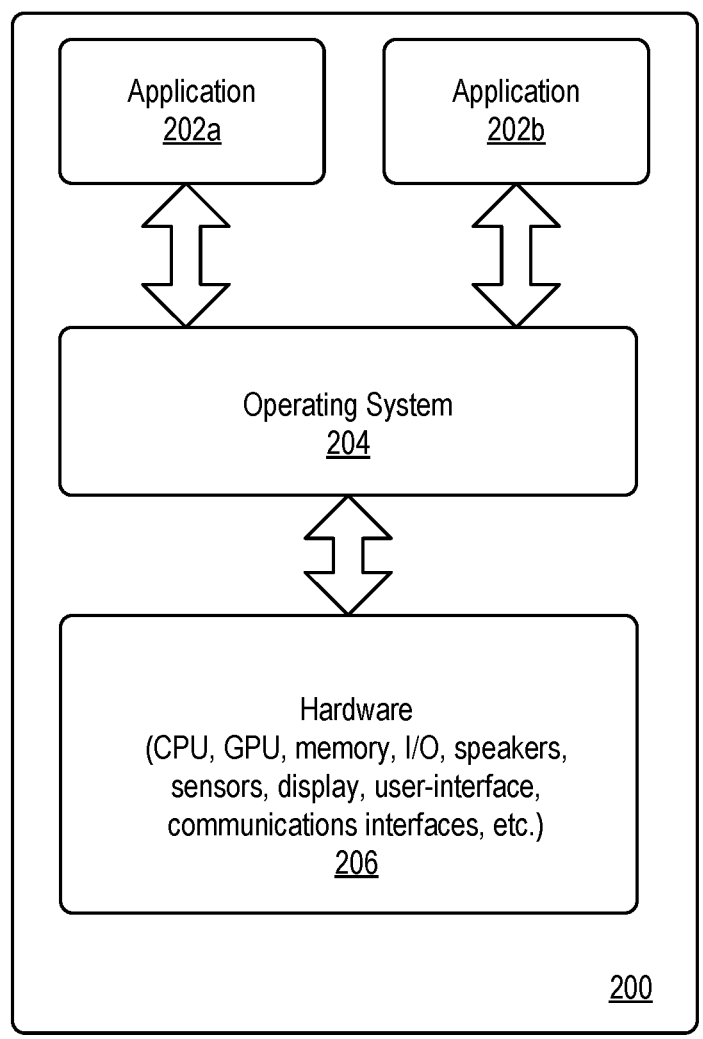
FIG. 2 shows an example client device according to some embodiments.

FIG. 2 shows an example client device 200 according to some embodiments. The client device 200 may be similar to or the same as client devices 116a-c shown and described in FIG. 1. In the example of FIG. 2, the client device 200 includes hardware 206 comprising: (i) one or more processors (e.g., a central processing unit(s) or CPU(s) and/or graphics processing unit(s) or GPU(s)); (ii) tangible non-transitory computer readable memory; (iii) input/output components (e.g., speaker(s), sensor(s), display(s), or other interfaces); and (iv) communications interfaces (wireless and/or wired). The hardware 206 components of the client device 102 are configured to run software, including an operating system 204 (or similar) and one or more applications 202a, 202b (or similar) as is known in the computing arts. One or more of the applications 202a and 202b may correspond to program code that, when executed by the one or more processors, cause the client device 200 to perform one or more of the functions and features described herein.

Prompting Entry of Relevant Disease Symptom, Factor, and Trigger Data

One common complaint among users of software-based healthcare management applications is that entering personal health data into the application tends to be tedious and cumbersome, particularly when the healthcare management application requires or otherwise relies upon multiple data points that must be collected multiple times every day. To overcome this and other limitations of many existing software-based healthcare management applications, some embodiments of the disclosed systems and methods include a client device (independently and/or directly or indirectly under the control of a server such as web server 102) configured to prompt patients to enter specific disease symptom/factor/trigger data at specific times or in response to specific events.

Some embodiments may employ the prompting feature/function described herein only for known or suspected disease triggers as a way to prioritize entry of characterization metrics for the known or suspected disease triggers. In these and other embodiments, a client device may still allow a patient to enter disease symptom/factor/trigger data separately from the prompting function.

In operation, a server system may determine, for a particular patient: (i) the specific disease symptom/factor/trigger data (including perhaps specific corresponding characterization metrics for the disease symptom/factor/trigger data) that the patient's client device(s) should prompt the patient to enter; and (ii) when the patient's client device(s) should prompt the patient to enter the specific disease symptom/factor/trigger data. Some embodiments may additionally or alternatively include the patient's client device(s) determining when to prompt the patient to enter certain disease symptom/factor/trigger data.

For example, if physical exercise has been determined to be a relevant disease factor/trigger for a particular patient, then after the patient's client device(s) (alone or in combination with the server system) determines or detects that the patient has engaged in some amount of physical exercise (e.g., based on accelerometer, gyroscope, GPS data, location data (showing that the patient was at a gym for example), heart rate monitor data), the client device(s) may prompt the patient to enter characterization metrics for the physical activity (e.g., type of exercise, duration, intensity) via a particular prompt configured to enter the specific characterization metrics for the specific disease factor or trigger of "physical exercise."

In another example, if the client device (alone or in combination with the server system) determines that the patient is at a restaurant (e.g., via location data), the client device may prompt the patient to enter what he or she ate. If one of the food items consumed by the patient is a disease factor or known disease trigger, the server may instruct the client device to prompt the patient to enter specific characterization metrics about the food consumed while the patient is still at the restaurant, or perhaps shortly after leaving the restaurant, while the information is still fresh in the patient's mind. Additionally, the client device (on its own or perhaps at the direction of the server) may also prompt the patient to enter additional characterization metrics for other disease factors or disease triggers that are suspected or known to interact with the food item to increase (or perhaps reduce) the patient's likelihood of experiencing the disease symptom.

In addition, once the client device and/or server know that the patient has experienced a known or suspected disease trigger (or perhaps even just a disease factor that has a somewhat high association with a disease symptom), the client device (on its own or perhaps at the direction of the server) may generate further prompts over the next few hours (or may be days) to collect additional disease symptom/factor/trigger data from the patient to closely monitor whether and the extent to which the known or suspected disease trigger had any effect on the disease symptom. For example, if caffeine is a known or suspected disease trigger, once the client and/or server know that the patient has consumed coffee, the client may generate further prompts in the future to ask the patient whether he or she has consumed any additional coffee or other caffeinated beverages. The client may also generate prompts to ask whether the patient has engaged in or experienced any other disease triggers that (for that patient) are known or suspected to interact with caffeine to increase or reduce the patient's likelihood of experiencing the disease symptom.

In this manner, the client and/or server uses information about an individual patient's disease symptoms, factors, and triggers and information about the patient's recent exposure to known or suspected disease factors and triggers to prompt the patient to enter relevant disease symptom/factor/trigger data that will be the most helpful for the server in determining: (i) which disease factors are most strongly associated with that patient's disease symptom(s); (ii) which disease factors have a sufficiently strong association with the patient's disease symptom(s) to be identified as a disease trigger for that patient, including, for example identifying the patient's disease factors/triggers that are most likely to cause the patient to experience a particular disease symptom and/or prevent the patient from experiencing a particular disease symptom; (iii) providing the patient's client device(s) with information describing the likelihood that the patient will experience (or not experience) a disease symptom in the near future, e.g., via a risk meter as shown and described with reference to FIGS. 9 and 11; and/or (iv) providing the patient's client device(s) with information on symptom/factor/trigger associations and disease trigger determinations, which the patient's client device(s) may in turn use to show the patient the impact that his or her conduct or environment might have on his or her near term likelihood of experiencing the particular disease symptom, e.g., via a trigger map as shown and described with reference to FIGS. 10 and 11.

Figure 3:
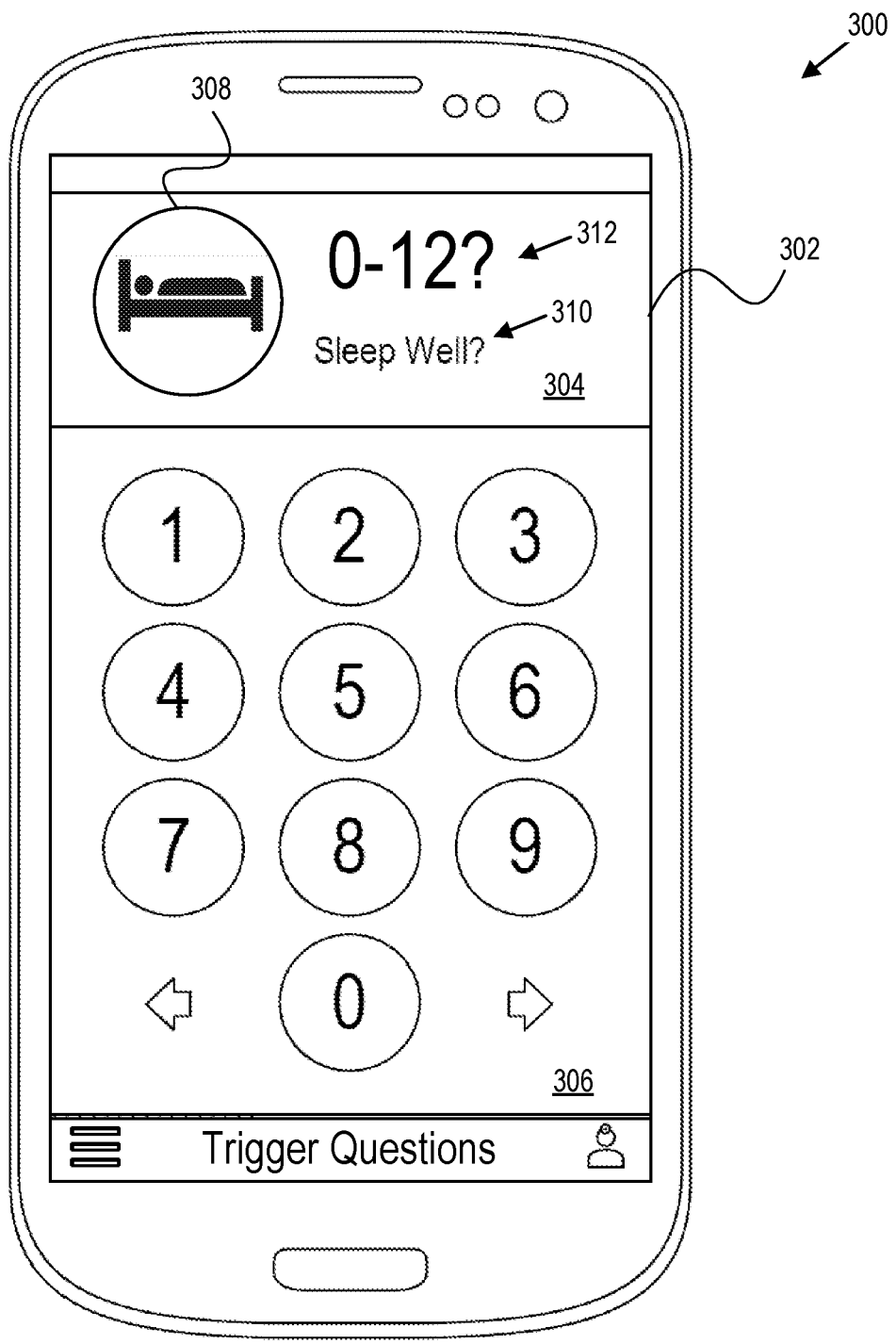
FIG. 3 shows an example GUI prompt on a client device according to some embodiments.

FIG. 3 shows an example GUI prompt 302 on a client device 300 according to some embodiments. The client device 300 may be the same as or similar to any of the client devices described herein, including but not limited to client devices 116*a-c* (FIG. 1) and/or client device 200 (FIG. 2).

The GUI prompt 302 includes a prompt field 304 and an input field 306 for receiving symptom/factor/trigger data from a patient. The prompt field 304 includes: (i) an icon 308 (or similar indication) that corresponds to at least one of a disease factor, disease trigger, or disease symptom; (ii) a short description 310 of the requested characterization metric(s); and (iii) a value range field 312 to indicate an acceptable range of values for the characterization metric(s).

The example shown in FIG. 3 assumes that "lack of sleep" is a disease trigger (or at least a disease factor for the patient) that is highly associated with the disease symptom (e.g., migraine headache in this case). In the example shown in FIG. 3, the icon 308 corresponds to "lack of sleep" (i.e., the disease factor/trigger), the short description 310 asks the user "Sleep Well?" and the value range field 312 shows that the user can enter any value between 0 and 12 as an acceptable range for the characterization metric, which for sleep is the number of hours slept. Other disease factors/triggers may have one or more different characterization metrics.

In some embodiments, the client 300 is configured display the GUI prompt 302 in response to a particular event. In the example shown in FIG. 3, the client 300 may display GUI prompt 302 in response to a wake-up alarm on the client 300. In other embodiments, the client 300 may display GUI prompt 302 in response to detecting that the patient began moving the client 300 (e.g., based on accelerometer, gyroscope, and/or GPS data) in the morning after a long period of inactivity, suggesting that the patient recently woke up. By prompting the user to enter the number of hours he or she slept right after determining, detecting, or otherwise inferring that the patient recently woke up in the morning, the client 300 encourages the patient to input data about the number of hours slept when the information is most-readily available.

If, for example, in response to GUI prompt 302, the patient entered a low number of hours (e.g., 4 hours) of sleep, and if lack of sleep is a known disease trigger for the patient (i.e., lack of sleep is highly associated with the patient experiencing a migraine headache in this example), then the client 300 (independently or perhaps at the direction of the server) may follow up with further GUI prompts throughout the day to gather relevant disease symptom/factor/trigger data from the patient that might be relevant in view of the patient's known disease trigger of "lack of sleep."

Because the patient reported a lack of sleep, the client device 300 may prompt the user later that morning to display GUI prompt 402 shown in FIG. 4, which illustrates another example GUI prompt on the client device 300 according to some embodiments.

The GUI prompt 402 includes a prompt field 404 and an input field 406 for receiving symptom/factor/trigger data from a patient. The prompt field 404 includes: (i) an icon 408 (or similar indication) that corresponds to at least one of a disease factor, disease trigger, or disease symptom; (ii) a short description 410 of the requested characterization metric(s); and (iii) a value range field 412 to indicate an acceptable range of values for the characterization metric(s).

Figure 4:
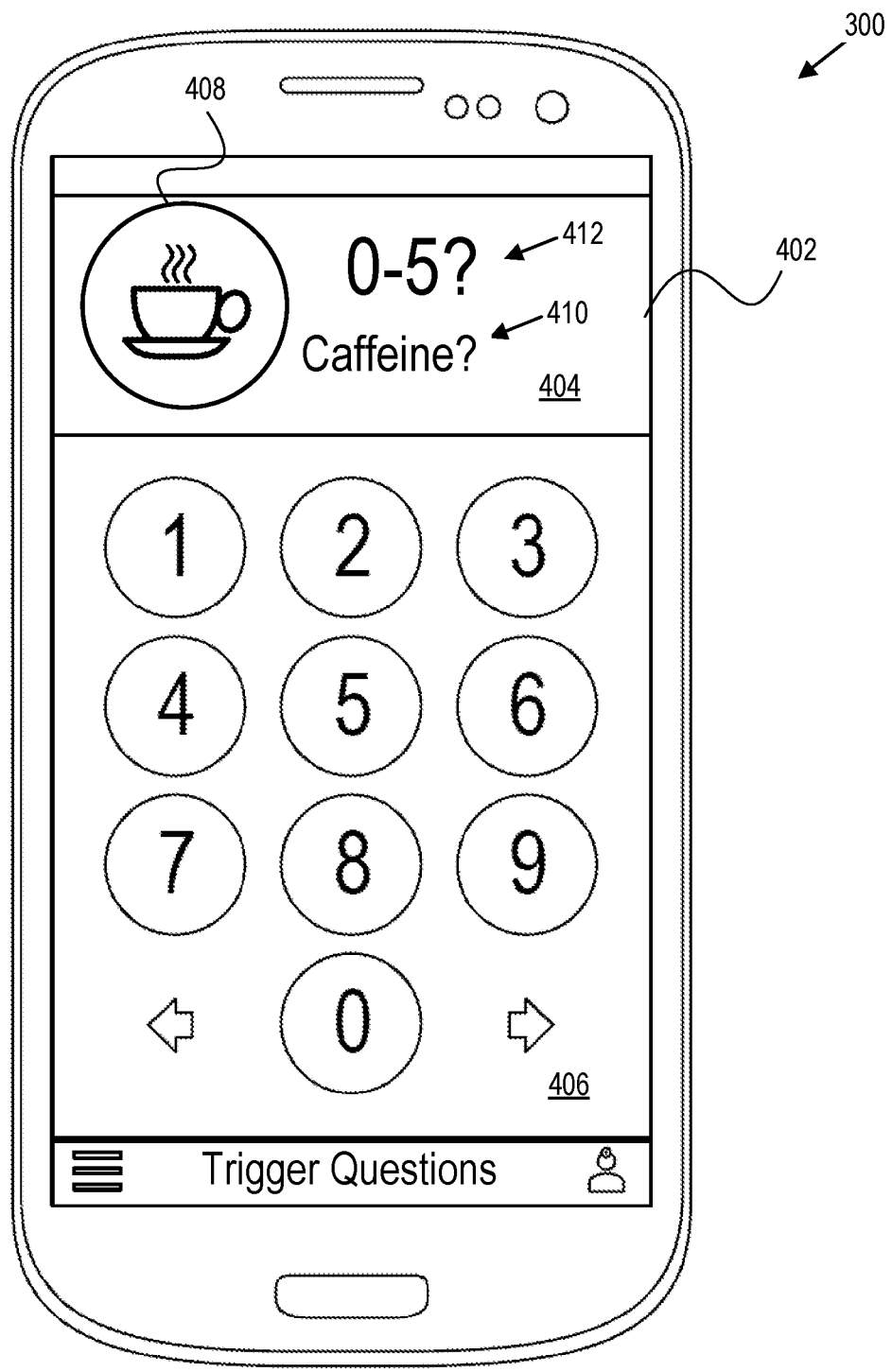
FIG. 4 shows an example GUI prompt on a client device according to some embodiments.

The example shown in FIG. 4 assumes that "caffeine" is a disease trigger (or at least a disease factor) for the patient. In the example shown in FIG. 4, the icon 408 corresponds to "caffeine" (i.e., the disease factor/trigger), the short description 410 asks the user "Caffeine?" and the value range field 412 shows that the user can enter any value between 0 and 5 as an acceptable range for the characterization metric, which for caffeine is the number of servings. Other disease factors/triggers may have one or more different characterization metrics.

In the example shown in FIG. 4, the client 300 may display GUI prompt 402 in response to the patient's earlier indication that he or she only had 4 hours of sleep the previous night. In this manner, the client device (individually or perhaps under control of a server) is selecting and displaying a later prompt (i.e., GUI prompt 402) based on disease factor/trigger data that the patient entered earlier (i.e., the lack of sleep indicated by the patient in response to GUI prompt 302). In other embodiments, the client 300 may display GUI prompt 402 in response to determining or detecting that the patient at a coffee shop (e.g., via GPS or other location data). By prompting the patient to enter the number of servings of caffeine he or she consumed in the morning shortly after learning that the patient only had 4 hours of sleep the previous night, the client 300 encourages the patient to input data about the number of servings of caffeine consumed (i) on a day when the patient is more likely to have consumed caffeine and (ii) at a time near when and/or location where the patient is likely to have consumed the caffeine, and thus when the disease trigger (caffeine consumption) information is most-readily available.

Figure 5:
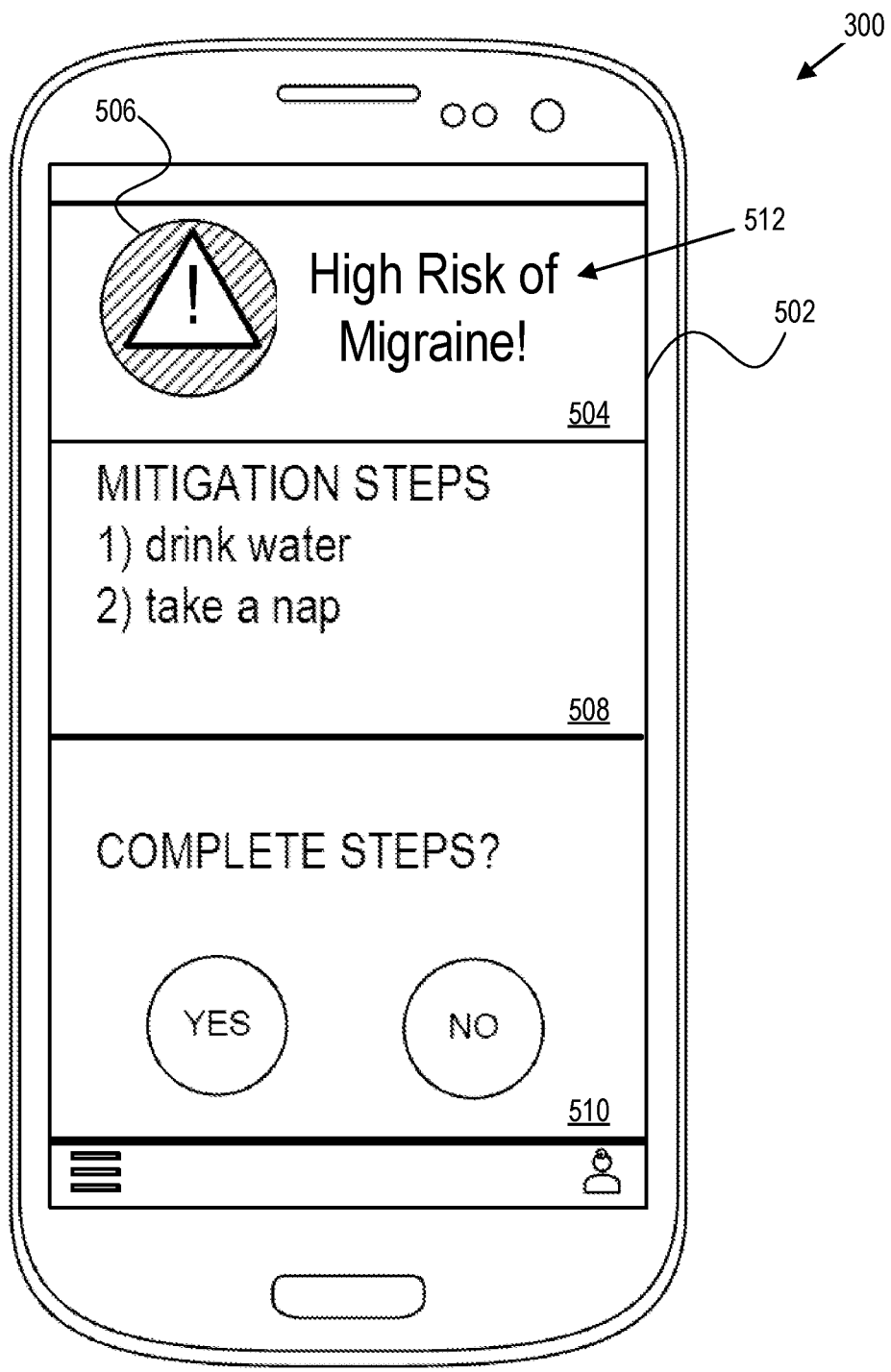
FIG. 5 shows an example notification within a GUI of a client device according to some embodiments.

In some embodiments, the client device may be configured to generate further prompts and/or notifications to encourage the patient to take one or more actions to reduce his or her likelihood of experiencing the disease symptom. FIG. 5 shows an example GUI prompt/notification displayed by client device 300 according to some embodiments.

The GUI prompt 502 includes a notification field 504, an instruction field 508, and an input field 510 for receiving patient input to confirm whether the patient followed the instructions/suggestions in the GUI prompt 502. The example shown in FIG. 5 assumes that the server system has previously determined that consuming water and taking a nap are both "protectors" for this particular patient (i.e., disease factors that tend to reduce this particular patient's likelihood of experiencing the disease symptom, which is a migraine headache in this example).

The notification field 504 includes: (i) an icon 506 (or similar indication) that corresponds to the type of notification; and (ii) a short description 512 of the notification. In the example of FIG. 5, the icon 506 corresponds to an "Alert" notification and the short description 512 states "High Risk of Migraine!" to inform the patient that he or she is over some threshold risk (e.g., over 70% or perhaps some other threshold risk) of experiencing a migraine headache based at least in part on the earlier received disease factor/trigger data, e.g., disease factor/trigger data received in response to GUI prompts 302 and 402 in FIGS. 3 and 4, respectively.

The instruction field 508 in this example includes "Mitigation Steps" that the patient can take to reduce his or her current likelihood of experiencing the disease symptom (e.g., migraine headache). Different disease symptoms for a patient may have one or more different mitigation steps, and different patients may have one or more different mitigation steps for the same disease symptom. In operation, the server determines mitigation steps for a particular patient and disease symptom based on the disease factors/triggers that are most likely to reduce the patient's likelihood of experiencing the disease symptom.

In some embodiments, the mitigation steps displayed in the instruction field 508 may be based on the particular disease triggers that are currently causing the patient to have a high risk of experiencing the disease symptom. The example shown here assumes that the server (via the procedures shown and described with reference to FIGS. 7 and 8) has determined that the mitigating factors of consuming water and taking a nap interact with the disease triggers of sleep deprivation and caffeine consumption.

In operation, different disease triggers may have different mitigating factors. For example, in one scenario, the server may have determined that (i) consuming chocolate and exposure to bright sunlight are disease triggers for a particular patient and (ii) exercise and consuming broccoli tend to reduce the likelihood that the patient's exposure to chocolate and bright sunlight will cause the patient to experience a disease symptom. In this scenario, if the patient has previously indicated that he or she has consumed chocolate and been exposed to bright sunlight, and if the server has in turn determined that the extent of the chocolate consumption and sunlight exposure are sufficient to increase the patient's risk of experiencing the disease symptom, the client may generate a GUI prompt/notification with mitigation steps that instruct the patient to consume broccoli and engage in physical exercise to reduce the patient's risk of experiencing the disease symptom.

Figure 6:
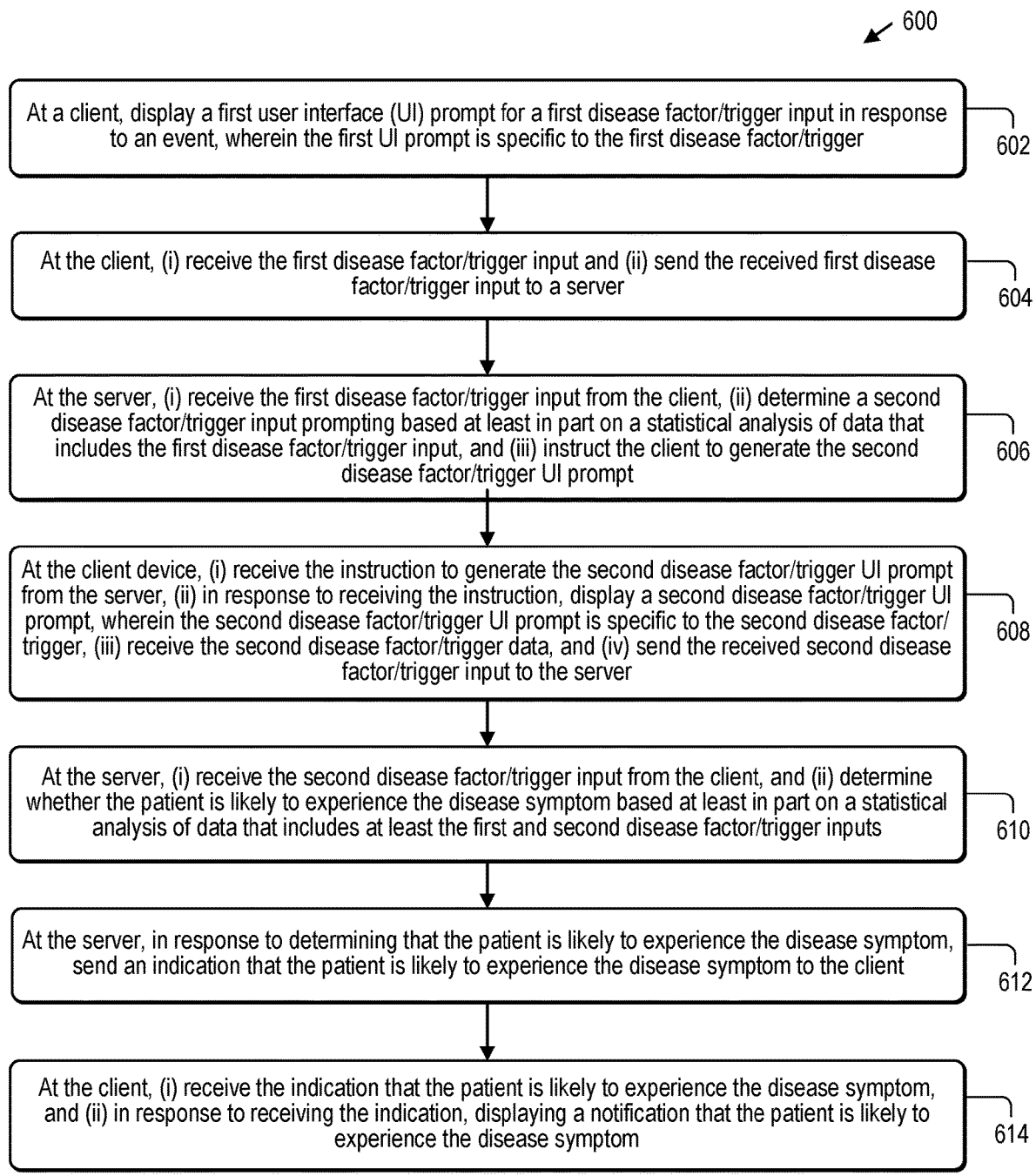
FIG. 6 shows an example method that includes generating GUI prompts for disease factor and/or disease trigger characterization metrics according to some embodiments.

FIG. 6 shows an example method 600 that includes generating GUI prompts for disease factor and/or disease trigger characterization metrics according to some embodiments. Although the blocks are illustrated in a sequential order, these blocks may in some instances be performed in parallel, and/or in a different order than those described herein. Also, the various blocks may be combined into fewer blocks, divided into additional blocks, and/or removed based on the desired implementation. Additionally, the example method 600 shows a client device performing some steps and a server performing other steps, but in alternative embodiments, some of the steps performed by a client in example method 600 may be performed by a server and vice versa.

Also, in method 600, each block may represent a module, a segment, or a portion of program code, which includes one or more instructions executable by a processor or computing device for implementing specific logical functions or steps in the method. The program code may be stored on any type of computer readable medium or memory, for example, such as a storage device including a disk or hard drive or other type of memory, such as flash memory or the like. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), and/or flash memory for example. The computer readable media may also be any other volatile or non-volatile storage systems. The computer readable medium may be considered a computer readable storage medium, for example, or a tangible storage device.

Example method 600 begins at block 602, where a client device displays a first user interface (UI) prompt for a first disease factor/trigger input in response to an event, wherein the first UI prompt is specific to the first disease factor/trigger. In operation, the client may be the same as or similar to any of the client devices disclosed herein.

At block 604, the client (i) receives the first disease factor/trigger input and (ii) sends the received first disease factor/trigger input to a server. In operation, the server may be the same as or similar to any of the server and/or server systems disclosed herein. In some embodiments, the client may send certain "high priority" disease factor/trigger inputs to the server in an expedited fashion. For example, a client device may send "high priority" disease factor/trigger inputs to the server immediately (or substantially immediately) in response to receiving such disease factor/trigger data (or a very short time thereafter) rather than holding and sending such disease factor/trigger data to the server at a later time.

At block 606, the server (i) receives the first disease factor/trigger input from the client, (ii) determines a second disease factor/trigger input prompting based at least in part on a statistical analysis of data that includes the first disease factor/trigger input, and (iii) instructs the client to generate the second disease factor/trigger UI prompt. In operation, the determination of the second disease factor/trigger input prompting may be based on the patient's response to the first disease factor/trigger prompt described in block 602 similar the examples described herein.

At block 608, the client device receives the instruction to generate the second disease factor/trigger UI prompt from the server, and in response to receiving the instruction, displays a second disease factor/trigger UI prompt, wherein the second disease factor/trigger UI prompt is specific to the second disease factor/trigger. After the client device receives second disease factor/trigger data from the patient via the second disease factor/trigger UI prompt, the client device sends the received second disease factor/trigger input to the server.

Next, at block 610, the server (i) receives the second disease factor/trigger input from the client, and (ii) determines whether the patient is likely to experience the disease symptom based at least in part on a statistical analysis of the patient's disease symptom/factor/trigger data that includes at least the first and second disease factor/trigger inputs.

A block 612, if the server determines that the patient is likely to experience the disease symptom based on the analysis conducted at block 610, then the server sends an indication that the patient is likely to experience the disease symptom to the client.

Finally, at block 614, the client, receives the indication that the patient is likely to experience the disease symptom from the server, and in response to receiving the indication, displays a notification that the patient is likely to experience the disease symptom, such as for example, the notification shown and described with reference to FIG. 5. In some embodiments, the notification may also include instructions for the client to perform actions to mitigate or reduce the patient's likelihood of experiencing the disease symptom.

Determining Associations between Disease Factors and Disease Symptoms

Figure 7:
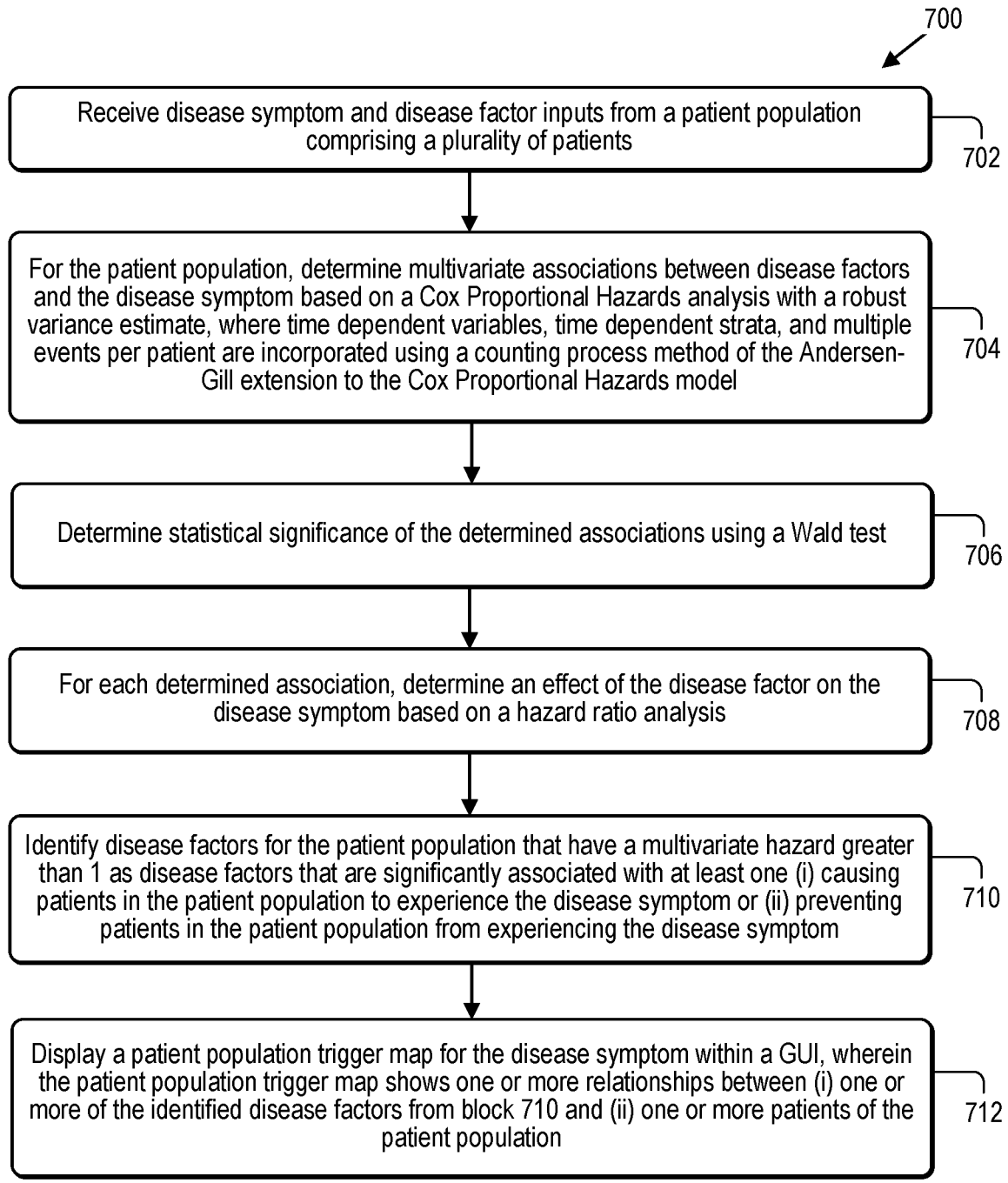
FIG. 7 shows an example method that includes determining associations and/or correlations between disease factors and a disease symptom for a patient population according to some embodiments.
Figure 8:
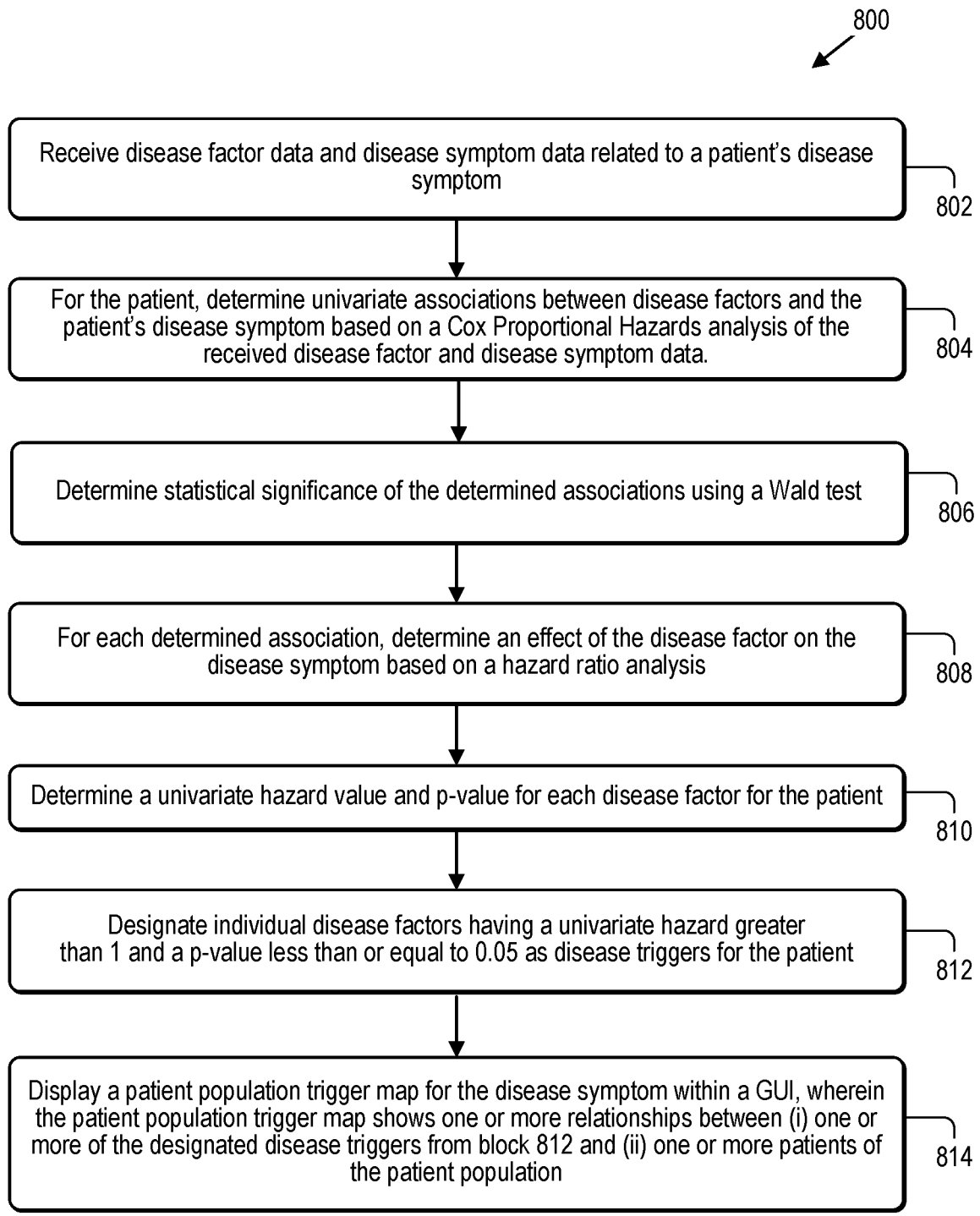
FIG. 8 shows an example method that includes determining associations and/or correlations between disease factors and/or disease triggers and a disease symptom for a patient according to some embodiments.

FIG. 7 shows an example method 700 that includes determining associations and/or correlations between disease factors and a disease symptom for a patient population according to some embodiments, and FIG. 8 shows an example method 800 that includes determining associations and/or correlations between (i) disease factors and/or disease triggers and (ii) a disease symptom for a patient according to some embodiments. Although the blocks are illustrated in a sequential order, these blocks may in some instances be performed in parallel, and/or in a different order than those described herein. Also, the various blocks may be combined into fewer blocks, divided into additional blocks, and/or removed based on the desired implementation. Additionally, the example methods 700 and 800 describe a server performing the method steps, but in other embodiments, a patient's client device may perform one or more of the method steps.

Also, in methods 700 and 800, each block may represent a module, a segment, or a portion of program code, which includes one or more instructions executable by a processor or computing device for implementing specific logical functions or steps in the method. The program code may be stored on any type of computer readable medium or memory, for example, such as a storage device including a disk or hard drive or other type of memory, such as flash memory or the like. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), and/or flash memory for example. The computer readable media may also be any other volatile or non-volatile storage systems. The computer readable medium may be considered a computer readable storage medium, for example, or a tangible storage device.

In some embodiments, example method 700 is performed by a server system. In such embodiments, the server that performs method 700 may be similar to or the same as any of the servers disclosed and described herein.

Method 700 begins at block 702, which includes receiving disease symptom and disease factor inputs from a patient population comprising a plurality of patients.

After receiving disease symptom and disease factor inputs from the patient population, method 700 advances to block 704, which includes determining (for the patient population) multivariate associations between disease factors and the disease symptom based on a Cox Proportional Hazards analysis with a robust variance estimate, where time dependent variables, time dependent strata, and multiple events per patient are incorporated using a counting process method of the Andersen-Gill extension to the Cox Proportional Hazards model. Some embodiments may alternatively use a logistic regression odds ratio analysis or other statistical methods and/or approaches.

Next, method 700 proceeds to block 706, which includes determining a statistical significance for each of the determined associations using a Wald test. Some embodiments may use alternative methods to determine a statistical significance for each of the determined associations.

After determining the statistical significance of each determined association in block 706, method 700 proceeds to block 708, which includes (for each determined association), determining an effect of the disease factor on the disease symptom based on a hazard ratio or similar analysis.

Next, block 710 includes identifying disease factors for the patient population that have a multivariate hazard greater than 1, and designating those identified disease factors as disease factors that are significantly associated with at least one (i) causing patients in the patient population to experience the disease symptom, or at least increasing the risk or likelihood that the patients in the patient population will experience the disease symptom, or (ii) preventing patients in the patient population from experiencing the disease symptom, or at least reducing the risk or likelihood that the patients in the patient population will experience the disease symptom.

Some embodiments of method 700 may additionally include block 712, which includes displaying a patient population trigger map for the disease symptom within a GUI. In operation, the patient population trigger map shows one or more relationships between (i) one or more of the identified disease factors from block 710 and (ii) one or more patients of the patient population. In some embodiments, the server system is configured to send data for displaying the patient population trigger map to a client device, such as any of the client devices shown and described herein. The patient population trigger map may be the same as or similar to the example patient population trigger maps shown and described herein with reference to FIGS. 12A and 12B.

FIG. 8 shows an example method 800 that includes determining associations and/or correlations between (i) disease factors and/or disease triggers and (ii) a disease symptom for a patient according to some embodiments. In some embodiments, method 800 is performed by a server system. In such embodiments, the server that performs method 800 may be similar to or the same as any of the servers disclosed and described herein.

Method 800 begins at block 802, which includes receiving disease factor data and disease symptom data for the individual patient. As described herein, the server system may receive disease factor data and disease symptom data from (i) the patient reporting his or her experience of the disease symptom data and disease factor data via inputs on a client device, (ii) the patient's client device detecting the patient's experience of the disease symptom or disease factors(s) via sensors on or in communication with the client device (e.g., bright lights detected by optical sensors, loud noises detected by microphones, physiological symptoms detected by physiological sensors in communication with the client device), and/or (iii) the server system receiving information about disease factor(s) in the area where the patient is located, e.g., via third party information sources.

Block 804 includes determining univariate associations between disease factors and the patient's disease symptom based on a Cox Proportional Hazards analysis of the received disease factor and disease symptom data. Some embodiments may alternatively use a logistic regression odds ratio analysis or other statistical methods and/or approaches.

At block 806, the server determines, for each determined association, a statistical significance of the determined associations using a Wald test. Some embodiments may use alternatively methods to determine a statistical significance for each of the determined associations.

Next, block 808 includes, for each determined association, determining an effect of the disease factor on the disease symptom based on a hazard ratio analysis or other similar analysis.

Then, at block 810, the server determines a univariate hazard value and p-value for each disease factor for the patient.

Next, at block 812, the server designates individual disease factors having a univariate hazard greater than 1 and a p-value less than or equal to 0.05 (or perhaps some other p-value threshold) as disease triggers for that particular patient. In some embodiments, the patient's identified disease triggers may be displayed within a trigger map for the patient, such as the trigger map shown and described herein with reference to FIG. 10.

Some embodiments may additionally include block 814, where the server displays a patient population trigger map for the disease symptom within a GUI. In operation, the patient population trigger map shows relationships between (i) one or more of the disease triggers determined in block 812 and (ii) one or more patients of the patient population. In some embodiments, the server system is configured to send data for displaying the patient population trigger map to a client device, such as any of the client devices shown and described herein. The patient population trigger map may be the same as or similar to the example patient population trigger maps shown and described herein with reference to FIGS. 12A and 12B.

Some embodiments may further include the server system determining whether it has identified all of a particular patient's disease triggers.

For example, when a particular patient has experienced the disease symptom on multiple occasions, the server system in some embodiments is configured to determine, for each occasion when the patient experienced the disease symptom, whether the patient experienced one or more of his or her previously identified disease triggers before experiencing the disease symptom. If, for multiple occasions when the patient has experienced the disease symptom, the server system determines that the patient experienced one or more of his or her previously identified disease triggers (identified according to the methods shown and described with reference to FIGS. 7 and 8 for example) before each occasion, then the server system may conclude that the server system has identified all of the patient's disease triggers, or at least identified all of the triggers that the patient routinely experiences.

In operation, the server system may determine whether the patient has experienced the disease symptom and whether the patient has experienced one or more of his or previously identified disease triggers via one of more of any of the methods disclosed herein, including but no limited to (i) the patient reporting his or her experience of the disease symptom and/or disease trigger(s) via inputs on a client device, (ii) the patient's client device detecting the patient's experience of the disease symptom and/or disease trigger(s) via sensors on or in communication with the client device (e.g., bright lights detected by optical sensors, loud noises detected by microphones, physiological symptoms detected by physiological sensors in communication with the client device), and/or (iii) the server system receiving information about disease triggers in the area where the patient is located, e.g., via third party information sources.

After concluding that it has identified all of the patient's disease triggers (or at least all of the triggers that the patient routinely experiences), the server system may inform the patient (e.g., by sending a message to the patient's client device) that the server system has identified all of the patient's disease triggers (or at least identified all of the triggers that the patient routinely experiences).

But if the server system determines that there are one or more occasions where the patient has experienced the disease symptom but the patient has not experienced one or more of his or her previously identified disease triggers (or at least not experienced one or more of the previously identified disease triggers within a threshold amount of time preceding his or her experience of the disease symptom, such as 12 to 24 or perhaps up to 48 hours before experiencing the disease symptom), then the server system may determine that it has not yet determined all of the patient's disease triggers (or at least not all of the triggers that the patient routinely experiences).

After concluding that it has not identified all of the disease triggers for the patient (or at least not all of the disease triggers that the patient routinely experiences), the server system may inform the patient (e.g., by sending a message to the patient's client device) that the patient has one or more as yet undetermined disease triggers. The server system may also select one or more new potential triggers (or disease factors) to track for the patient, or the patient may select one or more new potential triggers for the server system to track. In some embodiments, the server system may select the one or more new potential triggers from the set of patient population triggers described with reference to FIGS. 7, 12A, and/or 12B. The server system may also select one or more new potential triggers from a set of disease factors for the patient for which the server system has not established a sufficiently strong association with increasing the risk or likelihood that the patient will experience the disease symptom Regardless of the source of the new potential triggers (i.e., selected by the server system or the patient), the server system may send one or more messages to the patient's client device advising the patient to keep track of and report his or her exposure to the one or more new potential triggers. For example, in some embodiments, the server system may start periodically prompting the patient to enter characterization metrics associated with the one or more new potential triggers similar to the manner described with reference to FIGS. 3 and 4.

Additionally or alternatively, some embodiments may include the server system configuring the patient's client device to collect data regarding the patient's exposure to one or more potential triggers from one or more sensors on and/or in communication with the patient's client device.

Once the server system begins tracking the patient's exposure to the one or more new suspected triggers, the server system may employ the methods described with reference to FIG. 8 and elsewhere herein to determine whether each of the one or more new suspected triggers are actual triggers for the patient.

Disease Symptom Risk Meter

Figure 9:
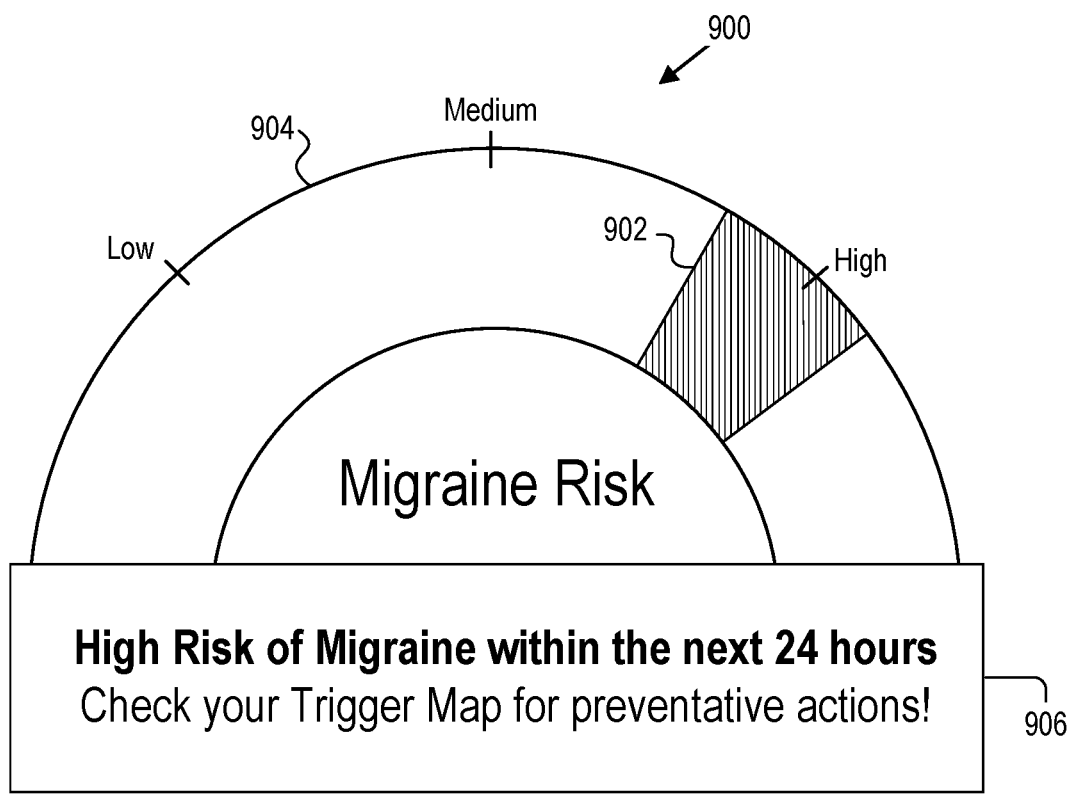
FIG. 9 shows an example risk meter displayed in a GUI on a client device according to some embodiments.

FIG. 9 shows an example risk meter 900 displayed in a GUI on a client device according to some embodiments. In operation, the client device that displays the risk meter 900 may be the same as or similar to any of the client devices disclosed and described herein.

Risk meter 900 includes a risk indication field 904 and a risk indicator 902. In operation, the risk indicator 902 may be positioned at a location within the risk field 904 to indicate a current likelihood (e.g., low, medium, high) that the patient will experience the disease symptom (i.e., a migraine headache in this example). Although the example risk meter 900 in FIG. 9 is shown in an oval "speedometer" type layout, other risk meter embodiments may have different layouts, such as, for example, (i) a linear, vertically-oriented risk indication field with a risk indicator that can be positioned higher or lower within the vertically-oriented risk indication field to indicate a higher or lower likelihood of experiencing the disease symptom or (ii) a linear, horizontally-oriented risk indication field with a risk indicator that can be positioned to the left or right within the horizontally-oriented risk indication field to indicate a lower or higher likelihood of experiencing the disease symptom.

In some embodiments, a server may determine whether the patient's current risk of experiencing the disease symptom is low, medium, or high (or perhaps other gradations or designations) by analyzing one or more of: (i) the patient's determined disease triggers, perhaps determined according to method 800 for example; (ii) the particular disease triggers that the patient has recently (e.g., within the last few hours or perhaps days) been exposed to or otherwise experienced, as reported by the patient, the patient's client device, and/or other sensors and/or information sources configured to monitor, collect and/or report the patient's disease trigger exposure to the server as described herein for example; and/or (iii) the determined strength of the association between (iii-a) the disease triggers that the patient has recently been exposed to or otherwise experienced and (iii-b) the disease symptom, as determined by method 800 for example.

In other embodiments, the server may provide the patient's client device with disease symptom/trigger data describing one or more of: (i) the patient's determined disease triggers, as determined by method 800, for example; (ii) the degree or strength of the association between each disease trigger and the disease symptom for the patient (e.g., based on the Cox Hazard Ratio, p-value, logistic regression odds ratio, or other quantification of the association); and/or (iii) a cumulative frequency and/or amount of the patient's exposure to the disease triggers within a recent time period (e.g., hours or perhaps days). And based on the disease symptom/trigger data received from the server (alone or perhaps in combination with more recent disease trigger data collected by the client device but perhaps not yet sent to the server), the client device may determine whether the patient's current risk of experiencing the disease symptom is low, medium, or high (or perhaps other gradations or designations) and display the determined current risk within the risk meter 900.

In operation, the risk indicator 902 is positioned at a location within the risk field 904 to indicate the current likelihood (e.g., low, medium, high) that the patient will experience the disease symptom (i.e., a migraine headache in this example). In some embodiments, the size of the risk indictor 902 may also reflect a degree of confidence (or perhaps margin of error) in the determined likelihood. In particular, when the determined likelihood (or risk estimate) is based on a smaller number of data points and a shorter history of disease symptom/factor/trigger data for the patient, the size of the risk indicator 902 may be larger to indicate a wider range of likelihoods, e.g., between 50-85% chance of experiencing the disease symptom. But when the determined likelihood (or risk estimate) is based on a larger number of data points and a longer history of disease symptom/factor/trigger data for the patient, the size of the risk indicator 902 may be smaller to indicate a smaller range of likelihoods, e.g., between 70-85% chance of experiencing the disease symptom.

In some embodiments, if the client and/or server (individually or in combination) determine that the patient is currently at a high risk of experiencing the disease symptom, then risk meter 900 may also generate an alert banner 906. In the example risk meter 900, the alert banner 906 informs the patient that there is a "High Risk of Migraine within the next 24 hours" and instructs the patient to "Check your Trigger Map for preventative actions!" Risk meters for different disease symptoms may have alert banners with different messaging and instructions. In some embodiments, a user touching, clicking, or otherwise interacting with the alert banner 906 may cause the client device to display the patient's trigger map within the GUI.

Some embodiments may also include the server system generating and sending electronic messages to a patient based on that patient's identified disease triggers/protectors. The messages may include one or more emails, text messages, in-app messages, or other types of electronic messages. In some embodiments, the system is configured to generate and send messages to a patient reminding the patient to avoid his or her identified disease triggers and/or encouraging the patient to engage in his or her identified disease protectors. In operation, the server system may send such reminders on a periodic or semi-periodic basis, for example, a few times a day, every day, a few times a week, once a week, or perhaps more or less often. Some embodiments may also include displaying such reminders as a notification with a risk meter such as risk meter 900. However, such reminders and notifications can be generated and sent to a patient's computing device independently and separate from functions performed in connection with a risk meter.

In operation, when a patient's computing device receives such a message or notification, the patient's computing device displays the message or notification within a GUI on the computer device. In some embodiments, some messages may further include software-based links that launch user interface screens for the patient to input his or her exposure to the disease trigger/protector identified in the message. For example, some messages may include software links that, when activated by the patient (e.g., by touching the link within the message or by touching a link on a notification within a risk meter), cause the client device to generate and display one or more GUI user interface screens similar to the ones shown and described with reference to FIGS. 3-5, thereby enabling the patient to input data characterizing his or her exposure to the disease trigger/protector identified in the message or notification.

Disease Trigger Map

Figure 10:
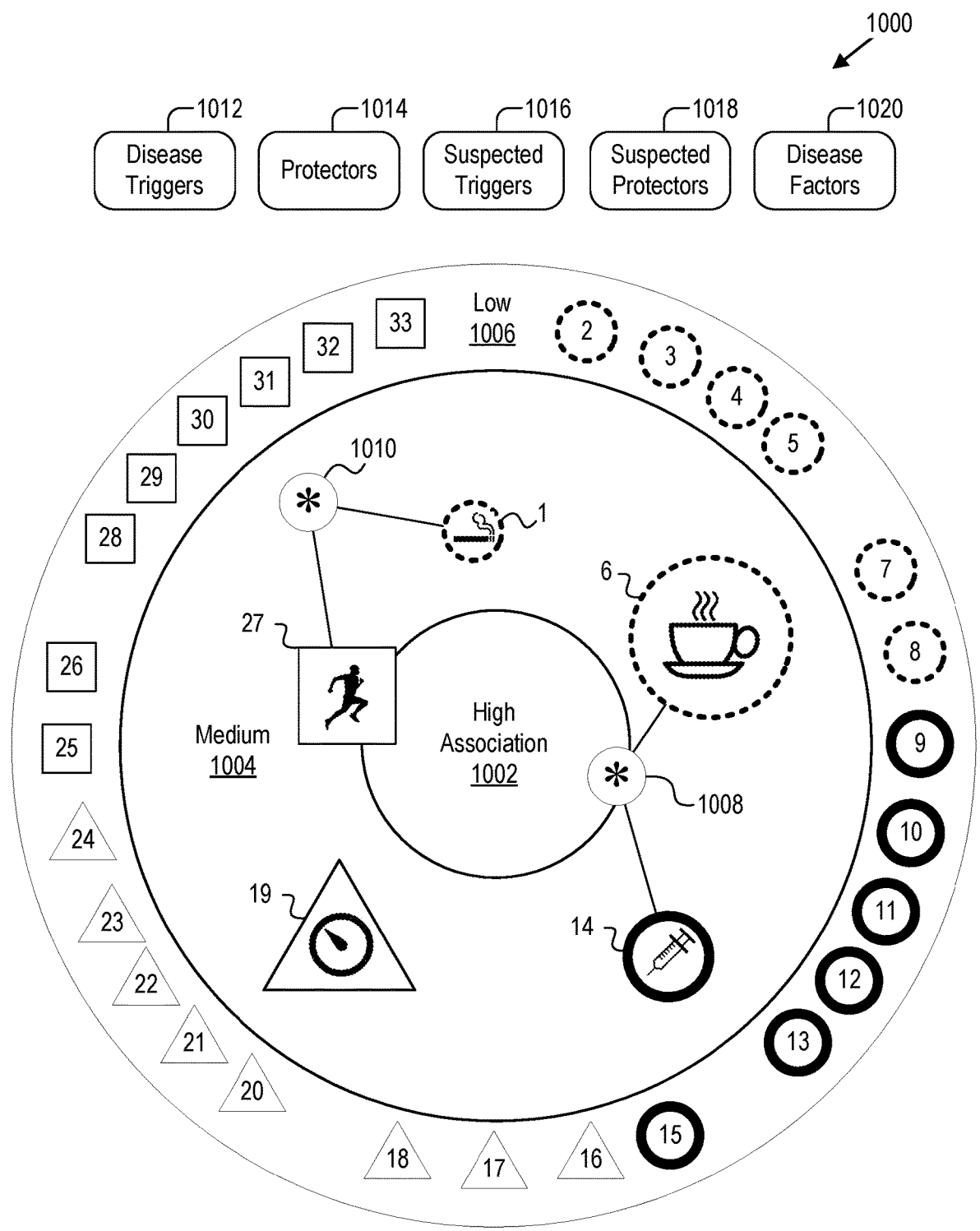
FIG. 10 shows an example disease trigger map displayed in a GUI on a client device according to some embodiments.

FIG. 10 shows an example disease trigger map 1000 displayed in a GUI on a client device according to some embodiments. In operation, the client device that displays the disease trigger map 1000 may be the same as or similar to any of the client devices disclosed and described herein.

The trigger map 1000 includes a plurality of trigger icons 1-33. In some embodiments, each trigger icon 1-33 corresponds to one of (i) a determined disease trigger for the patient, (ii) a determined protector for the patient, (iii) a suspected disease trigger (or suspected protector) for the patient, or (iv) a disease factor where there is currently insufficient data to determine whether the disease factor is a disease trigger, a suspected disease trigger, a protector, or a suspected protector for the patient.

As described earlier, (i) a disease factor is any event, exposure, action, or conduct related to and/or performed by a patient that has the potential to influence, affect, or cause the patient to experience a disease symptom, or in some cases, prevent the patient from experiencing a disease symptom, (ii) a disease trigger is a disease factor that has been determined through statistical analyses to have a sufficiently strong association with increasing the risk or likelihood that the patient will experience a particular disease symptom, as described herein, (iii) a protector is a disease factor that has been determined through statistical analyses to have a sufficiently strong association with decreasing the risk or likelihood that the patient will experience a particular disease symptom, as described herein, and a (iv) suspected disease trigger (or suspected protector) is a disease factor that has not yet been confirmed or verified to be a disease trigger (or protector), perhaps because of insufficient data to either (iv-a) confirm an association between the disease factor and increasing or decreasing the risk or likelihood that the patient will experience the disease symptom and/or (iv-b) quantify the degree or extent of association between the disease factor and the risk or likelihood of causing (or preventing) the disease symptom. In some embodiments, one or more of a patient's suspected disease triggers (or suspected protectors) may be derived through a patient survey where the patient lists his or her suspected disease triggers (or suspected protectors) along with a corresponding level of confidence (e.g., 1-10) that the suspected disease trigger increases (or suspected protector decreases) the risk or likelihood that the patient will experience the disease symptom. In some embodiments, one or more of the patient's suspected disease triggers (or suspected protectors) may be based on associations determined by the server system, where a suspected disease trigger (or suspected protector) is a disease factor with an association that is almost (but not quite) sufficiently strong to be deemed a disease trigger (or protector). For example, the association between the disease factor and a disease symptom may be just outside of one or more thresholds for declaring the disease factor to be a disease trigger (or protector), e.g., the association may have a Cox Hazard Ratio not quite greater than 1 and/or a p-value slightly more than 0.05.

In operation, a server system may determine whether a particular disease factor has a sufficiently strong association (or not) with a particular disease symptom based on a statistical analysis of disease symptom/factor/trigger input data relating to the patient (and/or perhaps the patient's patient population). For example, in some embodiments, the server system may determine the patient's disease triggers (or protectors) via methods 700 and 800 shown and described with reference to FIGS. 7 and 8, where the server (i) designates a specific disease factor as a disease trigger (or protector) for the patient in response to determining that an association between that specific disease factor and the disease symptom has a Cox Hazard Ratio greater than 1 and a p-value less than or equal to 0.05 and/or (ii) designates a specific disease factor as a suspected disease trigger (or suspected protector) for the patient in response to determining an association between that specific disease factor and the disease symptom has a Cox Hazard Ratio that is slightly less than 1 and has a p-value slightly greater than 0.05.

Additionally, different patients may have (i) different disease triggers, protectors, suspected triggers, suspected protectors, and disease factors, and (ii) different numbers of disease triggers, protectors, suspected triggers, suspected protectors, and disease factors. Therefore, different patients may have different trigger icons and different numbers of trigger icons in their individual trigger maps. Accordingly, in operation, a patient's trigger map may display more or fewer than 33 trigger icons.

In some embodiments, the trigger map may depict different classifications or types of trigger icons with different colors, outlines, shapes, or other distinguishing classification indications. For example, the trigger map may represent: (i) trigger icons corresponding to un-modifiable disease triggers with a first classification indication; (ii) trigger icons corresponding to modifiable disease triggers with a second classification indication; (iii) trigger icons corresponding to physical disease triggers with a third classification indication; and (iv) trigger icons corresponding to protectors with a fourth classification indication. The trigger map might also represent trigger icons corresponding to disease factors that have not been determined to be a disease trigger, protector, suspected trigger, or suspected protector with a fifth classification indication.

In example trigger map 1000, (i) trigger icons 1-8 have a dotted outline to indicate that they are classified as modifiable triggers, (ii) trigger icons 9-15 have a bolded outline to indicate that they are classified as un-modifiable triggers, (iii) trigger icons 16-24 are triangle-shaped to indicate that they are classified as physical or environmental triggers, and (iv) protector icons 25-33 are square-shaped to indicate that they are classified as protectors. Other examples with different (more or fewer) disease trigger classifications and different classification indications are possible as well.

The example trigger map 1000 also includes three regions: (i) a high association region 1002; (ii) a medium association region 1004; and (iii) a low association region 1006. The concentric circular bulls-eye arrangement of the different regions is only one example layout. Some embodiments may have concentric squares or adjacent square regions (e.g., quadrants or similar regions) and/or other shapes and layouts where different (more or fewer) regions correspond to different (more or fewer) determined association (e.g., high, medium, low, or other gradations) between the patient's disease symptom and the patient's disease factors/triggers.

In some embodiments, each trigger icon's position within the trigger map 1000 may be based on the degree or strength of the association between the trigger icon's corresponding disease trigger and the disease symptom for the patient (e.g., the Cox Hazard Ratio, p-value, or other quantification of the association).

As described earlier, in some embodiments, the server designates a disease factor as a disease trigger when the association between the disease factor and the disease symptom has a Cox Hazard Ratio greater than 1 and a p-value less than or equal to 0.05. In such embodiments, the position of a particular trigger icon within the trigger map is based on a standardized p-value of the univariate association between the disease trigger represented by the trigger icon and the disease symptom, which may be calculated according to the equation: (standardized p-value)=p-value/0.05. Disease triggers having a standardized p-value closer to 0 are highly associated with the disease symptom and will therefore be positioned closer to or inside of the High Association region 1002 near the center of trigger map 1000. Conversely, disease triggers having a standardized p-value closer to 1 are not as highly associated with the disease symptom and will therefore be positioned closer to or inside of the Low Association region 1006 of the trigger map 1000. Finally, disease triggers having a standardized p-value near 0.5 are positioned near the middle of the Medium Association region 1004 between the Low Association region 1006 and the High Association region 1002.

Likewise, as described earlier, in some embodiments, an individual patient may assign (via a patient survey or other form of patient input) a particular disease trigger (or protector), or perhaps a suspected disease trigger (or suspected protector) with a confidence level (e.g., 1-10), where (i) a disease trigger (or protector), or perhaps a suspected disease trigger (or suspected protector), with a lower confidence level indicates that the patient believes the disease trigger or protector is less likely to increase (or decrease) the patient's risk or likelihood of experiencing the disease symptom and (ii) a disease trigger (or protector), or perhaps a suspected disease trigger (or suspected protector), with a higher confidence level indicates that the patient believes the disease trigger or protector is more likely to increase (or decrease) the patient's risk or likelihood of experiencing the disease symptom. In such embodiments, the position of the disease trigger (or protector), or perhaps suspected disease trigger (or suspected protector), within the trigger map may be based on the patient-assigned confidence level, where the trigger map (i) displays disease triggers (or protectors), or perhaps suspected disease triggers (or suspected protectors) having a higher patient-assigned confidence level closer to the center of the trigger map and (ii) displays disease triggers (or protectors), or perhaps suspected disease triggers (or suspected protectors) having a lower patient-assigned confidence level further from the center of the trigger map (i.e., closer to the edge of the trigger map).

Also, in some embodiments, each trigger icon's size within the trigger map 1000 may be based on one or more of: (i) a cumulative frequency of the patient's exposure to the disease trigger corresponding to the trigger icon; and/or (ii) the amount of exposure and/or cumulative exposure (e.g., an amount of food or drug consumed). In some embodiments, the cumulative frequency or amount of exposure may be quantified by calculating the number of times or the amount of exposure over a timeframe.

Some embodiments may use different timeframes for different disease triggers based on an estimated time-decay of the effect that exposure to the disease trigger might have on the individual. For example, caffeine may stay in a patient's body for 6-8 hours after consumption, so a relevant timeframe for caffeine might be 6 or 8 hours because caffeine that was consumed 12 or 24 hours ago is likely no longer in the patient's body and therefore not likely to have any disease triggering effect. Similarly, physical exercise may have an effect on the patient's body for perhaps 36-48 hours, and thus, a relevant timeframe for physical exercise might be 36-48 hours. Indeed, exercise that the patient engaged in a week ago may have only a nominal effect (if any) on the patient's likelihood of experiencing the disease symptom.

In the example implementation shown in FIG. 10: (i) trigger icon 6 corresponds to "caffeine," which is a modifiable trigger because the hypothetical patient in this example can choose to consume or not consume caffeine; (ii) trigger icon 14 corresponds to "insulin," which for the hypothetical patient in this example is considered an unmodifiable trigger because the patient cannot safely forego insulin without jeopardizing his overall health and wellness, even though the amount of insulin received by the patient may vary from day to day if, for example, the patient receives insulin from an insulin pump configured to monitor the patient's blood sugar and administer insulation to maintain the patient's blood sugar at a safe, consistent level; (iii) trigger icon 19 corresponds to "low barometric pressure," which is physical/environmental trigger; (iv) protector icon 27 corresponds to "exercise," which is a protector for the hypothetical patient in this example; and (v) trigger icon 1 corresponds to "nicotine," which is a modifiable trigger because the hypothetical patient in this example can choose to not expose him or herself to nicotine.

In the example migraine implementation of FIG. 10, the "low barometric pressure" trigger icon 19 is positioned roughly in the middle of the medium association region 1004 of the trigger map 1000, which means that, for this patient, low barometric pressure is a disease trigger that has a "medium association" with migraine. Here, the size of the "low barometric pressure" trigger icon 19 is larger than the average size of the other trigger icons, which tells the patient not only that he or she has experienced low barometric pressure that day, but also that the extent of the low barometric pressure (based perhaps on duration and/or intensity) is may be greater than usual and possibly approaching a level where low barometric pressure might cause the patient to experience a migraine headache. In operation, the server may receive disease trigger input data regarding the patient's exposure to low barometric pressure from any one or more of: (i) a pressure sensor on the patient's client device (e.g., a smart phone); (ii) a pressure sensor communicatively coupled to the patient's client device and/or the server, and configured to report barometric pressure measurements to the patient's client device and/or the server; and/or (iii) a third-party information source, e.g., a local weather information service.

The server system may also be configured to determine whether various combinations of disease triggers might interact to increase the patient's likelihood of experiencing a disease symptom (or alternatively reduce the patient's likelihood of experiencing the disease symptom). In such a situation, the trigger map 1000 may indicate that a combination of disease triggers might be interacting to increase (or perhaps decrease) the patient's likelihood of experiencing the disease symptom with a trigger combination icon, such as the "caffeine-insulin" combination trigger icon 1008 or the "nicotine-exercise" combination trigger icon 1010.

For example, the "caffeine" trigger icon 6 is positioned roughly in the middle of the medium association region 1004 of the trigger map 1000, which means that, for this patient, caffeine is a disease trigger that has a "medium association" with migraine headache. The size of the "caffeine" trigger icon 6 is based on the number of servings that the patient has reported consuming within the last 6-8 hour window. Here, the size of the "caffeine" trigger icon 6 is larger than the average size of the other trigger icons, which tells the patient not only that he or she has consumed caffeine that day, but also that the extent of his or caffeine consumption is possibly approaching a level where caffeine might cause the patient to experience a migraine headache. The "insulin" trigger icon 14 is also positioned roughly in the middle of the medium association region 1004 of the trigger map 1000, which means that, for this patient, insulin has a "medium association" with migraine headache. The size of the "insulin" trigger icon 14 is no larger or smaller than the other trigger icons, which tells the patient that he or she has received some amount insulin (perhaps reported by an insulin pump communicatively coupled to the patient's client device and/or the server), but that the amount of insulin received thus far is unlikely, on its own at least, to cause the patient to experience a migraine headache.

However, in this example, the "caffeine" trigger icon 6 and the "insulin" trigger icon 14 are connected to a "caffeine-insulin" combination trigger icon 1008. The "caffeine-insulin" combination trigger icon 1008 is positioned almost entirely within the high association region 1002 of the trigger map 1000, which means that, for this patient, the combination of caffeine and insulin has a "high association" with migraine headache even though caffeine and insulin individually may each only have a "medium association" with migraine headache for this patient. In other words, caffeine and insulin interact to increase the patient's likelihood of experiencing a migraine headache.

Similarly, the "nicotine" trigger icon 1 is positioned roughly in the middle of the medium association region 1004 of the trigger map 1000, which means that, for this patient, nicotine is a disease trigger that has a "medium association" with migraine headache. The size of the "nicotine" trigger icon 1 is based on the number of relevant units of nicotine (e.g., the number of cigarettes) that the patient has reported consuming within the last few hours. Here, the size of the "nicotine" trigger icon 1 is no larger or smaller than the other trigger icons, which tells the patient that he or she has consumed some nicotine, but that the amount of nicotine consumed is unlikely, on its own at least, to cause the patient to experience a migraine headache. The "exercise" protector icon 27 is near the border between the medium association region 1004 and the high association region 1002 of the trigger map 1000, which means that, for this patient, exercise has a "medium-to-high" association with migraine headache. The size of the "exercise" protector icon 14 is somewhat larger than the other trigger icons, which tells the patient that he or she has recently engaged in exercise, and perhaps even a sufficient amount of exercise to reduce his or her likelihood of experiencing a migraine headache in the near term. In operation, the server may receive disease trigger data (or disease protector data in this case) regarding the extent and duration of the patient's exercise from any one or more of: (i) data entered manually by the patient; (ii) data received from one or more sensors on the patient's smart phone, e.g., accelerometers, gyroscopes, and/or GPS sensors; and/or (iii) data received from an external sensor communicatively coupled to one or both of the patient's smart phone or the server, e.g., sensors on a treadmill and/or a heart rate monitor.

Additionally, in this example, the "nicotine" trigger icon 1 and the "exercise" protector icon 27 are connected to a "nicotine-exercise" combination trigger icon 1010. The "nicotine-exercise" combination trigger icon 1010 is positioned near the border of the low association region 1002 of the trigger map 1000, which means that, for this patient, the combination of nicotine and exercise has a lower association with migraine headache than nicotine or exercise individually. In other words, exercise tends to reduce the patient's likelihood of experiencing a migraine headache based on nicotine exposure, or alternatively, that nicotine exposure perhaps reduces the protective effect of exercise for this patient.

Additionally, some trigger map embodiments may be configurable to selectively display one or more of the patient's (i) disease triggers, (ii) protectors, (iii) suspected triggers, (iv) suspected protectors, and/or (v) disease factors. In some embodiments, the trigger map may be configured to display one or more of the patient's disease triggers, protectors, suspected triggers, suspected protectors, and/or disease factors in response to receiving one or more commands via a GUI to display one or more of the patient's disease triggers, protectors, suspected triggers, suspected protectors, and/or disease factors.

The example trigger map 1000 shown in FIG. 10 also includes disease trigger selector icon 1012, protector selector icon 1014, suspected triggers selector icon 1016, suspected protectors icon 1018, and disease factors selector icon 1020. Other embodiments may have fewer selector icons than the ones shown in FIG. 10. Likewise, other embodiments may have different types of user input mechanisms (e.g., pull down menus, pop-up menus, or other mechanisms) via which to receive inputs to display data.

In operation, trigger map 1000 displays the patient's disease triggers when the disease triggers selector icon 1012 is activated. If none of the other selector icons 1014-1020 are activated, then the trigger map 1000 will only display the patient's disease triggers. Similarly, if the protectors selector icon 1014 is also activated while the disease trigger selector icon 1012 is activated, then the trigger map 1000 will display the patient's disease triggers and the patient's protectors, but the trigger map 1000 will not display the patient's suspected triggers, suspected protectors, or disease factors. And if the disease trigger selector icon 1012 is deactivated while the protector selector icon 1014 is still activated, then the trigger map 1000 will only display the patient's protectors. Likewise, if all of the selector icons 1012-1020 are activated, then the trigger map 1000 will show the patient's disease triggers, protectors, suspected triggers, suspected protectors, and factors. In this manner, the trigger map 1000 is configurable to display the patient's data based on which one or more of the selector icons 1012-1020 are activated or deactivated.

For example, the trigger map 1000 will display a patient's disease triggers but not display the patient's protectors, suspected triggers, suspected protectors, or disease factors when only the disease trigger selector icon 1012 is activated. Similarly, the trigger map 1000 will display the patient's protectors but not display the patient's disease triggers, suspected triggers, suspected protectors, or disease factors when only the protector selector icon 1014 is activated. Likewise, the trigger map 1000 will display the patient's suspected triggers but not display the patient's disease triggers, protectors, suspected protectors, or disease factors when only the suspected triggers selector icon 1016 is activated. In another example, the trigger map 1000 will display the patient's suspected protectors but not display the patient's disease triggers, suspected triggers, protectors, or disease factors when only the suspected protectors selector icon 1018 is activated. In yet another example, the trigger map 1000 will display the patient's disease factors but not display the patient's disease triggers, protectors, suspected triggers, or suspected factors when only the disease factors selector icon 1020 is activated.

Because the trigger map 1000 is configurable to display any one or more of the patient's disease triggers, protectors, suspected triggers, suspected protectors, and disease factors (in any combination), a patient (or perhaps a physician or other clinician working with the patient) using the trigger map 1000 can quickly display some or all of the patient's disease symptom/factor/trigger data within the trigger map 1000, thereby enabling the patient's disease symptom/factor/trigger data to be easily reviewed and analyzed. Some embodiments may additionally include the client device and/or the server storing a history of determined disease symptom/factor/trigger data to enable a patient to review how his or her exposure to various triggers and corresponding risk of experiencing the disease symptom changes (or at least has changed) on an hourly, daily, weekly, monthly, or even annual basis. Such embodiments may also include one or more additional selector icons (not shown) or similar user interface mechanisms (e.g., slider bars, pop-up menus, or other mechanisms) that configure the trigger map 1000 to display any one or more of the patient's disease triggers, protectors, suspected triggers, suspected protectors, and disease factors (in any combination) over different timeframes.

Figure 11:
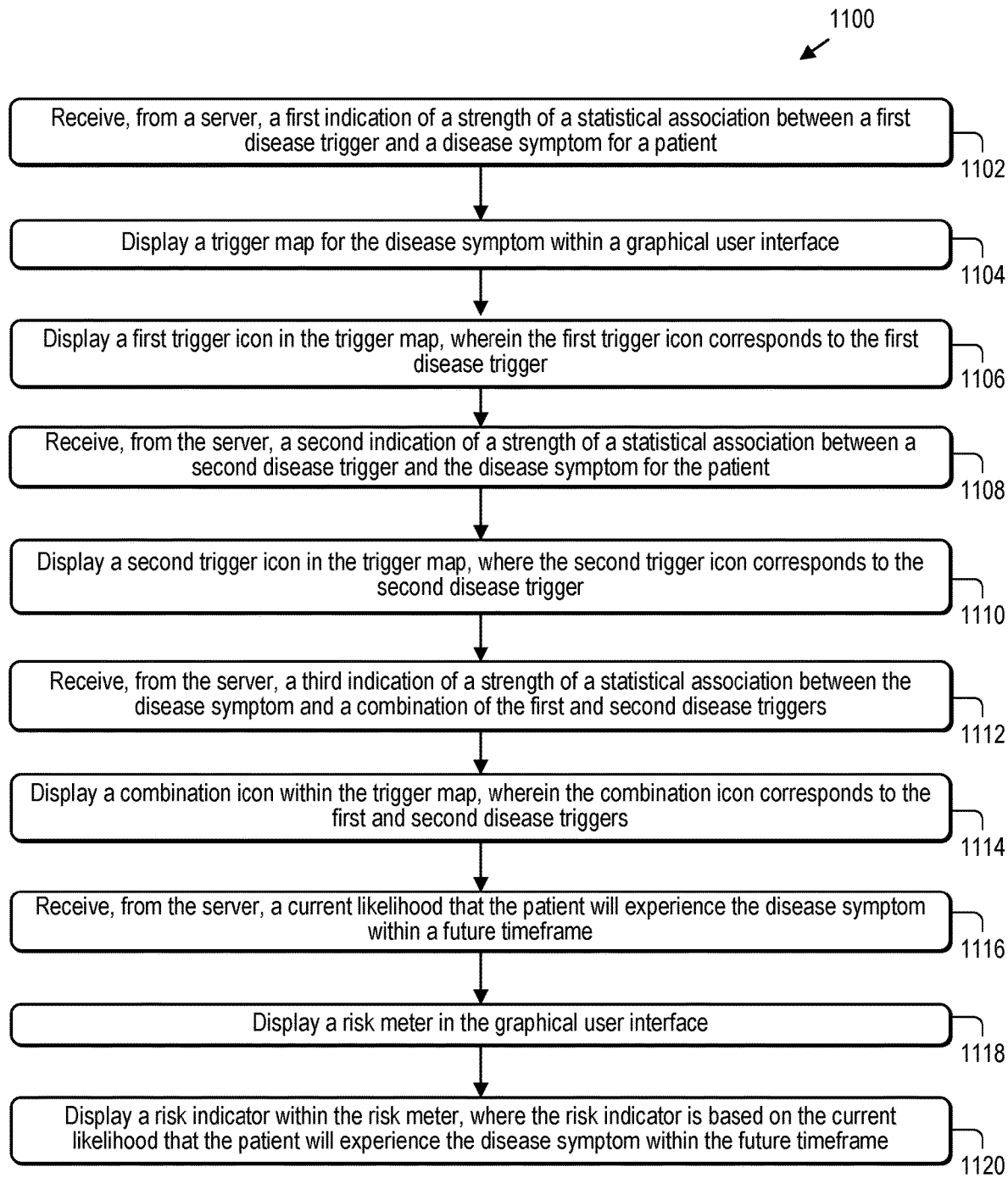
FIG. 11 shows an example method that includes displaying icons corresponding to disease triggers within a GUI on a client device according to some embodiments.

FIG. 11 shows an example method 1100 that includes displaying icons corresponding to disease triggers within a GUI on a patient's client device according to some embodiments. Although the blocks are illustrated in a sequential order, these blocks may in some instances be performed in parallel, and/or in a different order than those described herein. Also, the various blocks may be combined into fewer blocks, divided into additional blocks, and/or removed based on the desired implementation. Additionally, the example method 1100 shows a client device performing the method steps, but in other embodiments, a server may be configured to perform one or more of the method steps.

Also, in method 1100, each block may represent a module, a segment, or a portion of program code, which includes one or more instructions executable by a processor or computing device for implementing specific logical functions or steps in the method. The program code may be stored on any type of computer readable medium or memory, for example, such as a storage device including a disk or hard drive or other type of memory, such as flash memory or the like. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), and/or flash memory for example. The computer readable media may also be any other volatile or non-volatile storage systems. The computer readable medium may be considered a computer readable storage medium, for example, or a tangible storage device.

Method 1100 begins at block 1102, where the patient's client device receives, from a server, a first indication of a strength of a statistical association between a first disease trigger and a disease symptom for the patient. In operation the patient's client device may be the same as or similar any of the client devices described herein, and the server may be the same as or similar to any of the servers or server systems described herein.

In some embodiments, the first disease trigger comprises at least one of an event, exposure, action, or conduct related to and/or performed by the patient that has a potential to either (i) cause the patient to experience the disease symptom or (ii) prevent the patient from experiencing the disease symptom. Additionally, in some embodiments, the determined statistical association between the first disease trigger and the disease symptom (i.e., the first disease trigger-symptom association) has a Cox Hazard Ratio greater than 1 and a p-value less than or equal to a threshold p-value, and the first indication of the strength of the first disease trigger-symptom association for the patient is the p-value of the first disease trigger-symptom association divided by the threshold p-value.

At block 1104, the patient's client device displays a trigger map for the disease symptom within a graphical user interface. In some embodiments, the trigger map is the same as or similar to the trigger map shown and described with reference to FIG. 10.

Next, at block 1106, the patient's client device displays a first trigger icon in the trigger map, wherein the first trigger icon corresponds to the first disease trigger. In some embodiments, the position of the first trigger icon within the trigger map is based on the strength of the statistical association between the first disease trigger and the disease symptom, and the size of the first trigger icon is based on how much the patient has been exposed to the first disease trigger within a defined timeframe corresponding to the first disease trigger.

At block 1108, the patient's client device receives, from the server, a second indication of a strength of a statistical association between a second disease trigger and the disease symptom for the patient.

In some embodiments, the second disease trigger comprises at least one of an event, exposure, action, or conduct related to and/or performed by the patient that has a potential to either (i) cause the patient to experience the disease symptom or (ii) prevent the patient from experiencing the disease symptom. Additionally, in some embodiments, the determined statistical association between the second disease trigger and the disease symptom (i.e., the second disease trigger-symptom association) has a Cox Hazard Ratio greater than 1 and a p-value less than or equal to a threshold p-value, and the second indication of the strength of the second disease trigger-symptom association for the patient is the p-value of the second disease trigger-symptom association divided by the threshold p-value.

At block 1110, the patient's client device displays the second trigger icon in the trigger map, where the second trigger icon corresponds to the second disease trigger. In some embodiments, the position of the second trigger icon within the trigger map is based on the strength of the statistical association between the second disease trigger and the disease symptom, and the size of the second trigger icon is based on how much the patient has been exposed to the second disease trigger within a defined timeframe corresponding to the second disease trigger.

Next, at block 1112, the patient's client device receives, from the server, a third indication of a strength of a statistical association between the disease symptom and a combination of the first and second disease triggers. In some embodiments, the determined statistical association between the disease symptom and the combination of the first and second disease triggers (i.e., the disease trigger-combination-symptom association) has a Cox Hazard Ratio greater than 1 and a p-value less than or equal to a threshold p-value, and the first indication of the strength of the disease trigger-combination-symptom association for the patient is the p-value of the disease trigger-combination-symptom association divided by the threshold p-value.

At block 1114, the patient's client device displays a combination icon within the trigger map, wherein the combination icon corresponds to the combination of the first and second disease triggers. In some embodiments, the position of the combination icon within the trigger map is based on the third indication of the strength of the statistical association between the disease symptom and the combination of the first and second disease triggers, and the size of the combination icon is based on (i) how much the patient has been exposed to the first disease trigger within the defined timeframe corresponding to the first disease trigger and (ii) how much the patient has been exposed to the second disease trigger within the defined timeframe corresponding to the second disease trigger.

Block 1116 includes the patient's client device receiving, from the server, a current likelihood that the patient will experience the disease symptom within a future timeframe. In some embodiments, the likelihood is based at least in part on one or more of: (i) the strength of the statistical association between the first disease trigger and the disease symptom; (ii) the strength of the statistical association between the second disease trigger and the disease symptom; (iii) the strength of the statistical association between the disease symptom and the combination of the first and second disease triggers; (iv) how much the patient has been exposed to the first disease trigger within the defined timeframe corresponding to the first disease trigger; and/or (v) how much the patient has been exposed to the second disease trigger within the defined timeframe corresponding to the second disease trigger.

At block 1118, the patient's client device displays a risk meter in the graphical user interface. In some embodiments, the risk meter may be the same as or similar to the risk meter shown and described with reference to FIG. 9.

At block 1120, the patient's client device displays a risk indicator within the risk meter, where the risk indicator is based on the current likelihood that the patient will experience the disease symptom within the future timeframe. In some embodiments, the size of the risk indicator within the risk meter is based on a confidence level of the current likelihood that the patient will experience the disease symptom within the future timeframe.

Patient Population Trigger Map

Figure 12A:
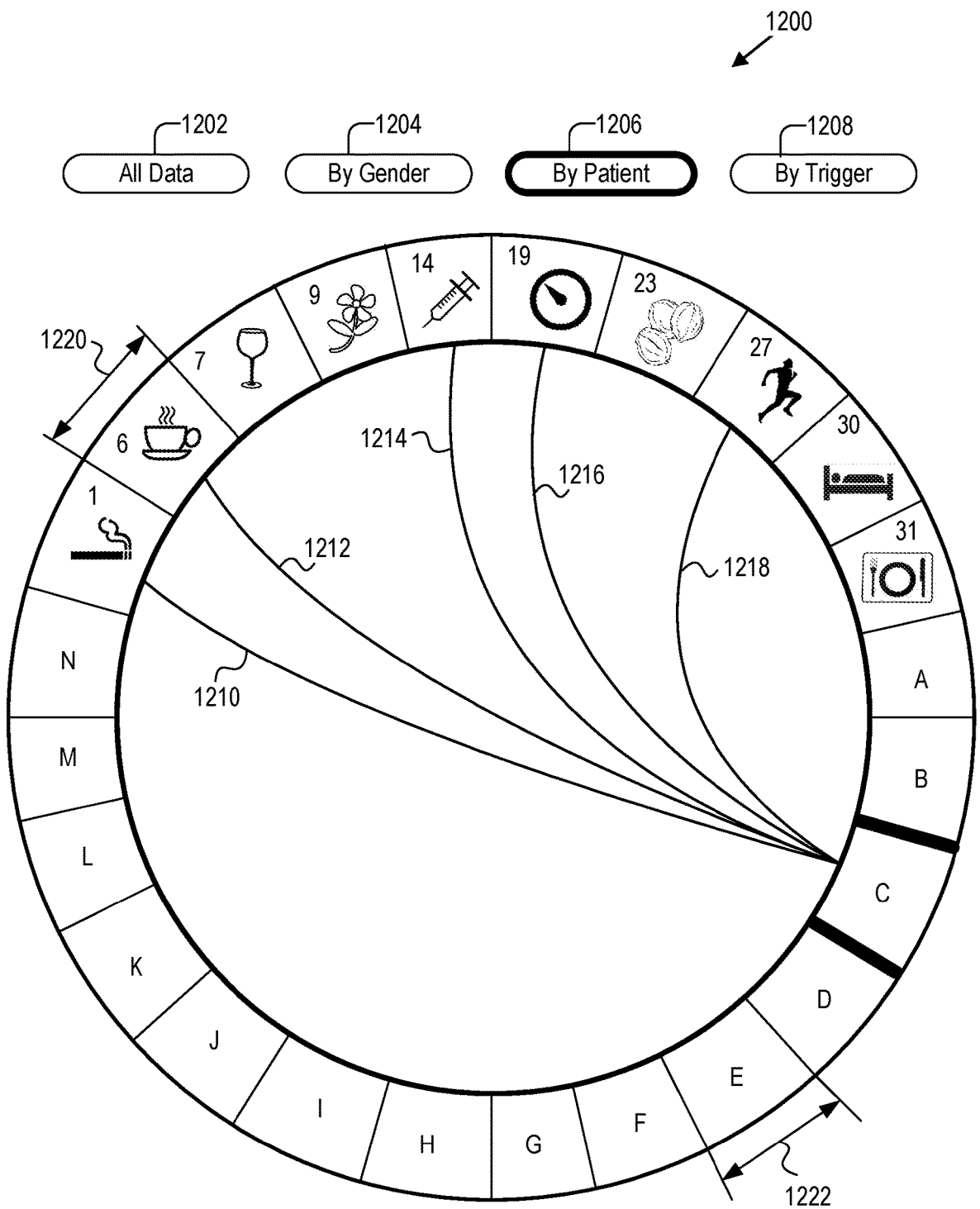
FIG. 12A shows an example patient population trigger map displayed in a GUI on a client device according to some embodiments.

FIG. 12A shows an example patient population trigger map 1200 displayed in a GUI on a client device according to some embodiments. In operation, the client device that displays the patient population trigger map 1200 within the GUI may be the same as or similar to any of the client devices disclosed herein. Also, in some embodiments, the client device that displays the patient population trigger map 1200 receives at least some of the patient and disease trigger data for displaying the patient population trigger map from a server system, such as any of the server systems disclosed and/or described herein.

The patient population trigger map 1200 shows relationships between (i) disease triggers (and protectors) and (ii) patients in a patient population. In operation, the server system has access to all of the disease triggers (and protectors) of every patient in the patient population because the server system has used disease factor and disease trigger data received from patients in the patient population to determine disease triggers for each patient in the patient population as described herein, with reference to FIGS. 7 and 8 and elsewhere. Because the system has disease trigger data for all the patients in the patient population, the server system can aggregate and organize the disease trigger data for the patient population, and, in combination with a client device, display disease trigger data for the patient population.

The example patient population trigger map 1200 includes: (i) an "All Data" icon 1202 that, when selected/activated by a user, configures the patient population trigger map 1200 to display all of the disease trigger data for all of the patients in the patient population; (ii) a "By Gender" icon 1204 that, when selected/activated by a user, allows the disease trigger data for the patient population to be filtered according to gender and configures the patient population trigger map 1200 to show disease trigger data for only males or only females in the patient population; (iii) a "By Patient" icon 1206 that, when selected/activated by a user, allows the disease trigger data to be filtered according to individual patients and configures the patient population trigger map 1200 to show disease trigger data for a selected subset of one or more patients in the patient population; and (iv) a "By Trigger" icon 1208 that, when selected/activated by a user, allows the disease trigger data to be filtered according to individual disease triggers and configures the patient population trigger map 1200 to show disease trigger data for a selected subset of one or more disease triggers.

Other embodiments may include one or more additional icons similar to icons 1202-1208 that, when selected/activated by a user, allows the disease trigger data for the patient population to be filtered according to other parameters and configures the patient population trigger map 1200 to show disease trigger data based on the filtered parameters. For example, the disease trigger data for the patient population can be sorted/filtered on one or more of a number of factors, including but not limited to patient, patient population, gender, age, age range, geographic location, occupation, employer, ethnicity, national origin, genetic marker, disease symptom, disease symptom severity, disease symptom frequency, disease trigger, disease protector, or any other data or characteristic about the patients, diseases, and/or disease triggers that is stored and/or accessible by the server system.

In the example shown in FIG. 12A, the patient population disease trigger data has been filtered by patient to show one or more relationships between (i) patient C in the patient population and (ii) patient C's disease triggers (and protectors) 1, 6, 14, 19, and 27.

As shown, patient C is one patient in a patient population comprising patients A-N. The patient population comprising patients A-N is shown in FIG. 12A for illustration only. In operation, and as described previously, a patient population may include more (and perhaps many more) or fewer patients than shown in FIG. 12A.

Patient C's disease triggers 1 (nicotine), 6 (caffeine), 14 (insulin), 19 (barometric pressure), and 27 (exercise) are described in more detail with reference to the trigger map 1000 shown and described with reference to FIG. 10. The disease triggers 1, 6, 14, 19, and 27 are shown in FIG. 12A for illustration purposes only. In operation a patient may have more (and perhaps many more) or fewer disease triggers than shown in FIG. 12A. In some embodiments, the disease triggers and protectors shown in the patient population trigger map 1200 comprise the union of all disease triggers and protectors for all patients in the patient population. When filtered by patient, the patient population trigger map 1200 may include a subset of one or more patients in the patient population.

In addition to disease triggers 1, 6, 14, 19, and 27, the patient population trigger map 1200 also shows disease triggers for patients in the patient population other than patient C. For example, patient population trigger map 1200 also shows disease trigger 7 (wine consumption), disease trigger 9 (pollen exposure), protector 23 (nut consumption), protector 30 (sufficient rest), and protector 31 (eating meals on time). These additional disease triggers (and protectors) are disease triggers (and protectors) for other patients in the patient population, i.e., patients A-B and D-N. In this view, patient C (or perhaps another patient or researcher) can see which disease triggers (and protectors) that patient C has in common with other patients in patient C's patient population (and/or perhaps relevant subset thereof).

For example, in patient population trigger map 1200: (i) relationship 1210 between patient C and trigger icon 1 shows that nicotine consumption is one of patient C's disease triggers; (ii) relationship 1212 between patient C and trigger icon 6 shows that caffeine consumption is another one of patient C's disease triggers; (iii) relationship 1214 between patient C and trigger icon 14 shows that insulin is another one of patient C's disease triggers; (iv) relationship 1216 between patient C and trigger icon 19 shows that low barometric pressure is yet another one of patient C's disease triggers; and (v) relationship 1218 between patient C and protector icon 27 shows that physical exercise is one of patient C's protectors. As noted, these are the same disease triggers and protectors shown and described with reference to FIG. 10.

In some embodiments, the size of the box in the patient population trigger map corresponding a particular disease trigger icon or disease protector icon (e.g., shown by line 1220) may be based on the number of patients in the patient population who share that particular disease trigger and/or protector, where boxes containing trigger icons for disease triggers (and/or protectors) that affect more patients in the population are larger than boxes containing trigger icons for disease triggers (and/or protectors) that affect fewer patients in the patient population.

In the example patient population trigger map 1200, size of the boxes surrounding the disease triggers and protectors are all more or less equal, which means that each of disease triggers and protectors shown affect approximately the same number of patients in the patient population (or at least the display subset of the patient population comprising patients A-N).

In an example where caffeine is a disease trigger for all of the patients in the patient population, the size of the box surrounding trigger icon 6, as shown by line 1220, might be substantially larger (or at least somewhat larger) than the size of other boxes surrounding other disease trigger/protector icons that affect less than all of the patients in the patient population.

Similarly, in some embodiments, the size of the box corresponding to a particular patient (e.g., the size of the box corresponding to patient E shown by line 1222) may correspond to the number of disease triggers and/or protectors for that patient. In the example patient population trigger map 1200, the size of the boxes corresponding to each of patients A-N are all more or less equal, which means that each of patients A-N have approximately the same number of disease triggers and/or protectors. In an example where patient E has more disease triggers than other patients in patients in the patient population, the size of the box corresponding to patient E, as shown by line 1222, might be substantially larger (or at least somewhat larger) than the size of other boxes corresponding to other patients in the patient population who have fewer disease triggers and/or protectors than patient E.

Also, in the patient population trigger map 1200, the relationships 1210-1218 between patient C and disease triggers 1, 6, 14, and 19 (and protector 27) are shown as lines, but in other embodiments, the relationships may be illustrated in other ways, such as with colors, bolding, shading, animation, and/or other methods of displaying relationships between icons and information within a GUI.

Additionally, in some embodiments, the patient population trigger map 1200 may also indicate the degree or strength of the association (as previously described in detail with reference to FIGS. 7-8 and 10 and elsewhere) between a disease trigger icon's corresponding disease trigger and a patient's disease symptom via a variety of ways. For example, in embodiments like FIG. 12A where relationships 1210-1218 are indicated with lines, thicker (i.e. heavier weight) lines may indicate a stronger association whereas thinner lines indicate a weaker association. Alternatively, differently colored or differently patterned lines, or different types of bolding, shading, animation, or other indications may indicate comparatively stronger or weaker associations.

Figure 12B:
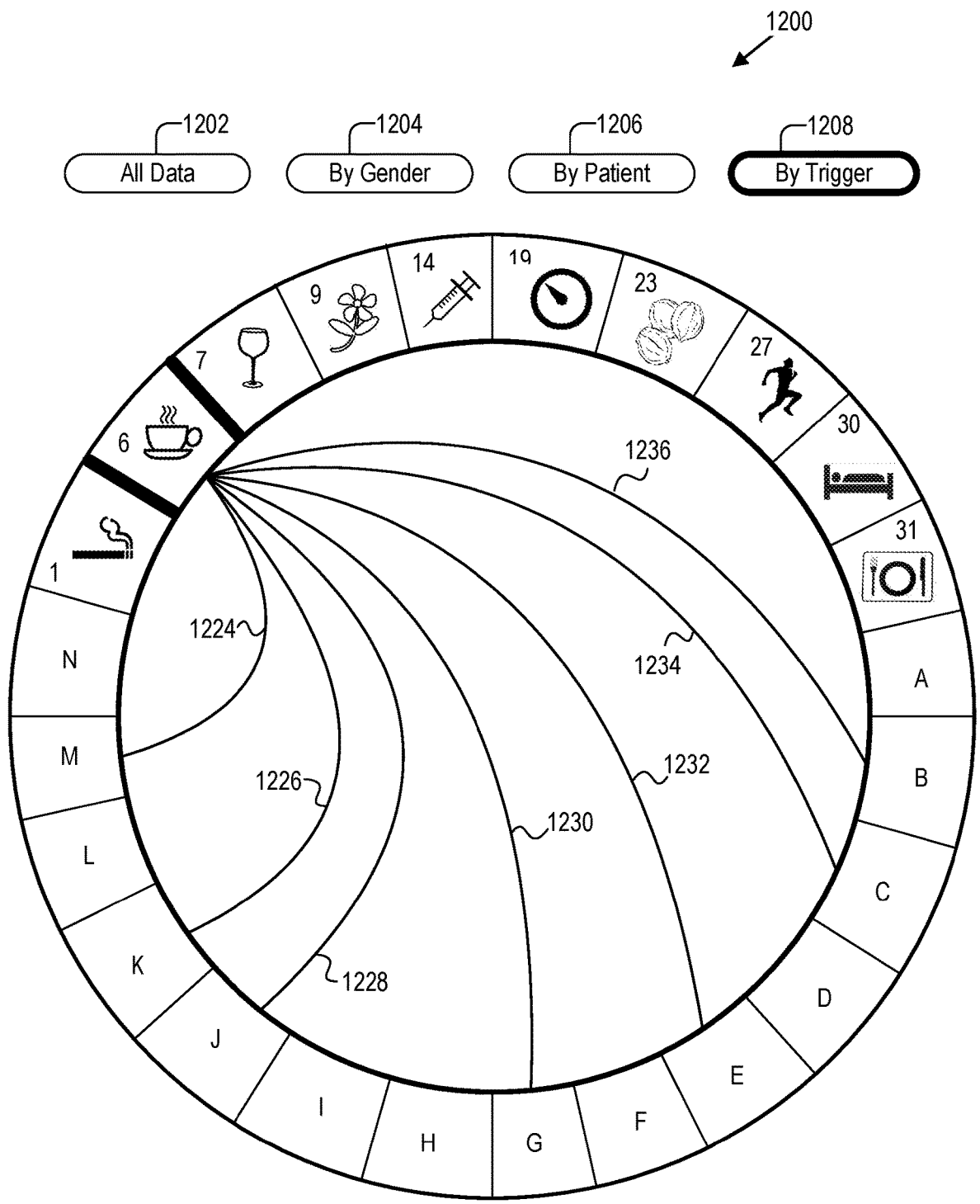
FIG. 12B shows a different arrangement of the example patient population trigger map shown in FIG. 12A, according to some embodiments.

FIG. 12B shows a different arrangement of the example patient population trigger map 1200 shown in FIG. 12A, according to some embodiments.

In FIG. 12B, the trigger data for the patient population comprising patients A-N has been filtered according to disease triggers. For example, the "By Trigger" icon 1208 has been selected/activated, and the data has been filtered to indicate the patients from the patient population who share caffeine as a disease trigger. For example, in patient population trigger map 1200: (i) relationship 1224 between trigger icon 6 and patient M shows that caffeine consumption is one of patient M's disease triggers; (ii) relationship 1226 between trigger icon 6 and patient K shows that caffeine consumption is also one of patient K's disease triggers; (iii) relationship 1228 between trigger icon 6 and patient J shows that caffeine consumption is one of patient J's disease triggers; (iv) relationship 1230 between trigger icon 6 and patient G shows that caffeine consumption is one of patient G's disease triggers; (v) relationship 1232 between trigger icon 6 and patient E shows that caffeine consumption is one of patient E's disease triggers; (vi) relationship 1234 between trigger icon 6 and patient C shows that caffeine consumption is one of patient C's disease triggers (as noted previously with reference to FIGS. 10 and 12A); and (vii) relationship 1236 between trigger icon 6 and patient B shows that caffeine consumption is also one of patient B's disease triggers.

Also, in the patient population trigger map 1200, the relationships 1224-1236 between disease triggers 6 and patients B, C, E, G, J, K, and M are shown as lines, but in other embodiments, the relationships may be illustrated in other ways, such as with colors, bolding, shading, animation, or other methods of displaying relationships between icons and information within a GUI. Additionally, in some embodiments, the patient population trigger map 1200 may also indicate the degree or strength of the association (as previously described in detail with reference to FIGS. 7-8 and 10 and elsewhere) between a disease trigger icon's (e.g., trigger icon 6) corresponding disease trigger (i.e. caffeine consumption) and the disease symptom for each patient via a variety of ways. For example, in embodiments like FIG. 12B where relationships 1224-1236 are indicated with lines, thicker lines may indicate a stronger association whereas thinner lines indicate a weaker association. Alternatively, differently colored or differently patterned lines, or different types of bolding, shading, animation, or other indications may indicate comparatively stronger or weaker associations.

In these and other patient population trigger map embodiments, a patient and/or researcher may review and consider (i) how a patient's disease triggers compare with other patients in the patient's patient population, (ii) whether and the extent to which certain disease triggers may be more or less prevalent within a particular patient population, and/or (iii) whether and the extent to which a patient may have more or fewer disease triggers as compared to other patients in that patient's patient population. As mentioned previously, a patient population may include many (hundreds, thousands, or more) of patients who all share one or more similarities (e.g., the same age or age range, same gender, same ethnicity, same national origin, suffer from the same disease, have the same allergies, have the same genetic markers, and/or perhaps other similarities), and some patients may be members of multiple patient populations.

Facilitating Communication and Information Sharing between Patients

Some embodiments may further include electronic messaging capabilities (e.g., individual email, group email, individual text messaging, group text messaging, group discussion boards, chat rooms, or other known messaging capabilities) that enable patients in the patient population to communicate and/or share disease symptom and disease trigger information with each other. In some embodiments, the messaging system may be configured to enable a patient to communicate with one or more other patients in the patient population to share information and/or recommendations about personal experiences with their own disease symptoms and disease triggers/protectors so that patients can experiment with recommended triggers/protectors and document their experience with those same triggers/protectors via any of the disease trigger data entry mechanisms described herein.

In some embodiments, a server system (such as the server system shown and described with reference to FIG. 1) may recommend that two or more patients communicate or at least share their personal disease symptom and/or disease trigger information with each other. The recommendation to the two or more patients may be based on one or more similarities or shared traits between the patients, such as whether the patients (i) have the same disease symptom(s), (ii) experience the same disease symptom with the same or similar severity or frequency, (iii) experience some of the same disease triggers and/or protectors, (iv) are the same gender or age, (v) live in the same area, (vi) have the same or similar occupations, (vii) are the same ethnicity or share the same ethnic background, (viii) share some of the same genetic markers, and/or (ix) share other traits in common. In operation, similarities between patients may be determined based on one or both of patient demographic information, patient account information, and/or patient disease trigger information stored and/or accessible by the server system. Some embodiments may enable patients to exchange messages or engage in other types of communications with other patients in an anonymized fashion, such as with patient numbers or similar aliases, although anonymized communication is not required.

Figure 13:
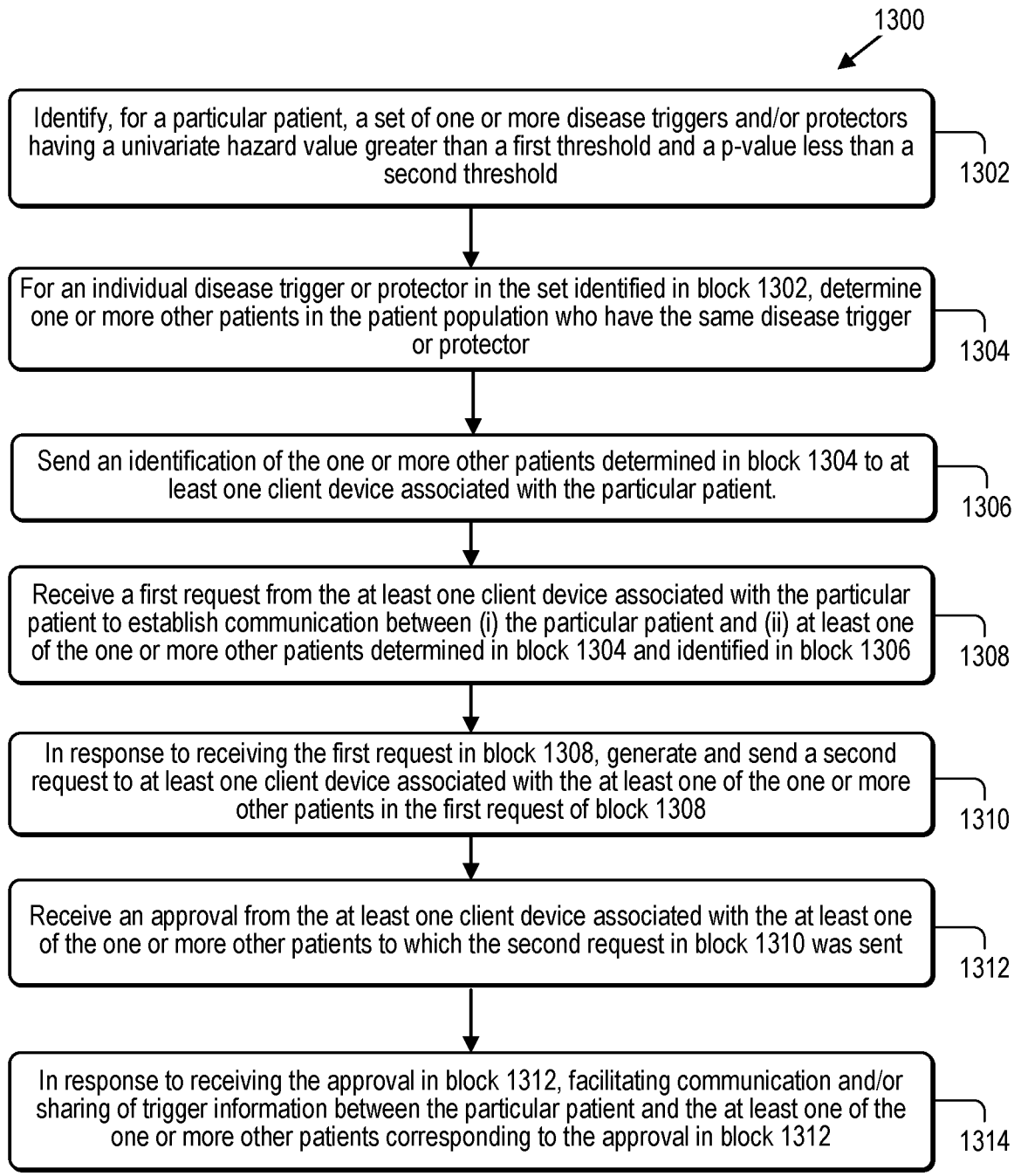
FIG. 13 shows a method of facilitating communication and information sharing between patients having one or more disease triggers, protectors, or other traits in common, according to some embodiments.

FIG. 13 shows a method 1300 of facilitating communication and information sharing between patients having one or more disease symptoms and/or disease triggers or protectors in common, according to some embodiments. Although method 1300 focuses on an example where patients have one or more disease triggers in common, method 1300 could be adapted for use with patients that have other traits in common, such as any of the patient traits described herein.

Method 1300 begins at block 1302 where the server system identifies, for a particular patient (the source patient), a set of one or more disease triggers and/or protectors having a univariate hazard value greater than a first threshold and a p-value less than a second threshold. As described in more detail with reference to FIGS. 7 and 8, in some embodiments, the system is configured to designate individual disease factors having a univariate hazard value greater than 1 and a p-value less than or equal to 0.05 as disease triggers (or protectors) for the source patient. In such embodiments, the first threshold corresponding to the univariate hazard value is preferably some value greater than 1 and the second threshold corresponding to the p-value is preferably some value less than 0.05. In this manner, the system is identifying the disease triggers and/or protectors that have the strongest association with a disease symptom for the source patient.

After identifying the disease triggers and protectors having the strongest association with a particular disease symptom for the source patient, method 1300 advances to block 1304 where, for an individual disease trigger or protector in the set identified in block 1302, the system determines a trigger group for the source patient. The trigger group includes one or more other patients in the patient population who have the same disease trigger or protector. Because patient populations may contains hundreds or even thousands of patients (or perhaps more), it may be helpful for the system to narrow the potential number of patients in a trigger group for a source patient. Therefore, in some embodiments, the source patient's trigger group may be limited to only other patients (i) who have the same trigger (or protector) and (ii) for whom that same trigger (or protector) has a univariate hazard value greater than the first threshold and a p-value less than the second threshold. Thus, in such embodiments, the other one or more patients in the source patient's determined trigger group in block 1302 are patients for whom the trigger (or protector) is also strongly associated with the disease symptom.

Next, method 1300 advances to block 1306, where the server system sends an identification of the one or more other patients determined in block 1304 (i.e., the determined trigger group) to at least one client device associated with the source patient. The source patient's client device may be the same as or similar to any of the client devices described herein. In operation, the identification sent in block 1306 may take many forms, including but not limited to an email or text notification, a popup window or banner displayed within the source patient's trigger map (FIG. 10) or the patient population trigger map (FIGS. 12A and 12B), or other notification. For example, within the source patient's trigger map (FIG. 10) or the patient population trigger map (FIGS. 12A and 12B), the source patient's client device may generate a pop-up style (or similar) message or prompt within a GUI that says, for example, "Trigger X is also a strong trigger for 55 other patients. Would you like to share your experiences with Trigger X with some of these patients?" where Trigger X is one of the disease triggers or protectors identified at block 1302. When the source patient activates such a prompt within the GUI, the source patient's client device may display, within the GUI, a subset of one or more patients from the trigger group (block 1304) for the source patient to select as target patient(s) with whom to (i) communicate and/or (ii) share disease symptom and/or disease trigger or factor information. The subset of patients from the trigger group to display to the source patient may be based on one or more factors, including but not limited to other patient(s) from the trigger group who (i) have one or more other traits in common with the source patient (e.g., same occupation, live in same city or town, same gender, same age range, same genetic markers, etc.), (ii) have the highest (or perhaps higher than average) univariate hazard value and lowest (or perhaps lower than average) p-value for "Trigger X" (see above) among the patients in the trigger group, and/or (iii) have similar disease symptom frequency and/or intensity. The server system may select the subset of patients from the trigger group based on other patient similarities and/or differences as well or perhaps based on how much information each of the other patients is willing to share, which may be based on a user profile or similar information stored in the server system about the other patients. In operation, the source patient's client device receives from the source patient, a designation of which patients in the subset of patients from the trigger group (i.e., which target patients) with whom to (i) initiate communications and/or (ii) share disease symptom and/or disease trigger information.

In some embodiments, the system may additionally or alternatively ask the source patient if he or she wishes to join a discussion group focused on that particular disease trigger (or perhaps a group of disease triggers), or perhaps a discussion group with patients that have one or more other similar traits, e.g., patients with the same gender, patients within the same age rage, patients with the occupation, patients living in the geographic area, or other patient similarities. The system may also enable patients to initiate communications and disease symptom and trigger data sharing from within discussion groups.

At block 1308, the server system receives a first request from the at least one client device associated with the source patient (i.e., one of the devices to which the identification in block 1306 was sent) to establish communication between (i) the source patient and (ii) at least one of the target patients. Additionally, or alternatively, the first request may include a request to share the source patient's disease symptom and/or disease trigger information the target patient(s). In operation, the source patient's client device sends the first request to the server system in response to receiving some selection of one or more target patients from the source patient, for example, via inputs received by the client device from the source patient.

In some embodiments, the first request may also indicate a level of anonymity associated with the communication request and/or an amount or type of information that the source patient is willing to share with other patients. For example, the source patient may request to communicate with the target patient(s), but only identify himself or herself with his or her patient number or similar alias rather than the source patient's real name or user ID. Similarly, the source patient may request that the system only share some the source patient's trigger information and/or disease symptom history with the target patient(s). For example, the source patient may wish to share information about the particular disease trigger that he or she has in common the target patient(s) but perhaps not share information about other disease triggers that he or she does not share with the target patient(s).

At block 1310, and in response to receiving the first request in block 1308, the server system generates and sends a second request to at least one client device associated with the at least one of the one or more other patients in the first request of block 1308 (i.e., the one or more target patients). In operation, this second notification informs each of the one or more target patients that the source patient wishes to communicate and/or share information about disease triggers (and perhaps other patient traits) that the source patient and the target patient(s) have in common. The second notification can take many forms, including but not limited to an email or text notification, a popup window or banner displayed within the source patient's trigger map (FIG. 10) or the patient population trigger map (FIGS. 12A and 12B), or other notification.

At block 1312, the server system receives an approval from a client device associated with the at least one of the one or more other patients to which the second request in block 1310 was sent (i.e., one of the target patients). In operation, a target patient's client device sends such an approval to the server system in response to receiving an indication (e.g., an input or response) from the target patient that the target patient agrees to communicate and/or share disease symptom/trigger information with the source patient. In some embodiments, the approval may also include a level of anonymity with which the target patient wishes to communicate with the source patient. For example, a target patient may agree to communicate with the source patient, but only identify him or herself with his or her patient number or similar alias rather than the target patient's real name or user ID. Similarly, the target patient may agree to only share some of his or her trigger information and disease symptom history with the source patient. For example, the target patient may wish to share only information about the particular disease trigger that he or she has in common with the source patient, but perhaps not share information about other disease triggers that he or she does not share with the source patient.

At block 1314, and in response to receiving the approval in block 1312, the server system facilitates communication and/or sharing of disease symptom (and/or disease trigger) information between the source patient and the at least one of the one or more other patients corresponding to the approval(s) received in block 1312. In operation, once the source patient and the trigger patient(s) have agreed to communicate and share disease symptom and/or disease trigger information, the source and trigger patient(s) can view details regarding each other's disease symptom and/or disease trigger history that are stored and/or accessible by the server system (to the extent that the source patient and target patient(s) have agreed to share such information). Such disease symptom and disease trigger history may include the frequency and intensity of disease symptoms, the frequency and extent of exposure to disease triggers and protectors, and/or any other additional information about the source and trigger patients stored or at least accessible by the server system.

Additionally, once the patients are in communication with each other and able to see each other's disease symptom and disease trigger data, the patients may be able to recommend ways of managing their disease symptoms and disease trigger exposure and/or perhaps protectors to consider. Similarly, if one patient discovers that a certain protector is particularly effective for him or her either in general or with regard to a particular trigger, that patient can share the protector with other patients who can then test it out for themselves and log their results in the system for analysis as described herein.

In some embodiments, the server system may restrict communication and/or information sharing between two patients to the strictest level agreed to between the two patients (e.g., a first and second patient). For example, if the first patient wishes to share only disease trigger information and not share disease symptom information, then the first and second patients will only be able to see each other's disease trigger information even if the second patient has agreed to share both disease trigger and disease symptom information. Similarly, if the first patient agrees to share only one month of disease trigger data with another patient, the first and second patients will only be able to see one month of each other's disease trigger information even if the second patient has agreed to share six months of disease trigger information. In this manner, the system encourages more open information sharing between patients because a patient will only receive a type, level, or amount of information from other patients to the extent that he or she has agreed to share that same type, level, or amount of information with other patients.

In operation, enabling patients in the patient population to communicate with each other to share information and/or recommendations about personal experiences with their own disease symptoms and disease triggers/protector in the above-described manner may prompt patients to experiment with and/or recommended triggers/protectors and document their experience with those triggers/protectors in the system, thereby providing the system with more disease trigger information for analysis and helping patients gain a better understanding of their own disease symptoms and triggers through the exchange of such information.

CONCLUSION

While particular aspects and embodiments are disclosed herein, other aspects and embodiments will be apparent to those skilled in the art in view of the foregoing teaching. For example, while the embodiments and examples are described with respect to migraine headaches, the disclosed systems and methods are not so limited and may be applicable to a broad range of disease symptoms and related disease factors and disease triggers. The various aspects and embodiments disclosed herein are for illustration purposes only and are not intended to be limiting, with the true scope and spirit being indicated by the following claims.

What is claimed is:

1. A method of configuring a graphical user interface of a client device, the method comprising:
    providing, by way of the graphical user interface of the client device, a plurality of input prompts corresponding to a set of disease triggers that are determined to be relevant to a user of the client device experiencing a disease symptom;
    receiving, by way of the graphical user interface of the client device, a plurality of inputs relating to the disease symptom and the set of disease triggers relevant to a user of the client device experiencing the disease symptom;
    receiving, by the client device from a server based on the plurality of inputs, a first indication of a statistical association strength between a first disease trigger in the set of disease triggers and the disease symptom for the user of the client device, wherein the server is configured to use a processor to identify the set of disease triggers for the user and to track the plurality of inputs received by the client device to determine associations between the set of disease triggers and the disease symptom; and responsive to receiving the first indication of the strength of the statistical association between first disease trigger and the disease symptom, configuring the graphical user interface of the client device to indicate a risk of the user experiencing the disease, wherein indicating the risk of experiencing the disease symptom comprises displaying, by the client device, a trigger map for the disease symptom within the graphical user interface, wherein the trigger map includes trigger icons representing disease triggers associated with the disease symptom, and wherein displaying the trigger map within the graphical user interface comprises:

displaying, by way of the graphical user interface of the client device, a first trigger icon within the trigger map, wherein the first trigger icon corresponds to the first disease trigger, wherein the position of the first trigger icon within the trigger map is based on the received first indication of the statistical association strength between the first disease trigger and the disease symptom, and wherein a first trigger icon size is based on how much the user has been exposed to the first disease trigger within a defined timeframe corresponding to the first disease trigger, wherein the first trigger icon size and position within the graphical user interface indicates a risk of experiencing the disease symptom associated with (i) the statistical association strength between the first disease trigger and the disease symptom and (ii) how much the user has been exposed to the first disease trigger.

2. The method of claim 1, wherein the disease trigger comprises at least one of an event, exposure, action, or conduct related to and/or performed by the user that has a potential to cause the user to experience the disease symptom.

3. The method of claim 1, further comprising:
receiving, by the client device from the server, an indication of a statistical association strength between a protector and the disease symptom for the user, wherein the protector comprises at least one of an event, exposure, action, or conduct related to and/or performed by the user that can prevent the user from experiencing the disease symptom; and
displaying a protector icon corresponding to the protector within the trigger map, wherein a protector icon position within the trigger map is based on the received indication of the statistical association strength between the protector and the disease symptom, and wherein a protector icon size is based on how much the user has been exposed to the protector within a defined timeframe corresponding to the protector.

4. The method of claim 1, wherein the determined statistical association between the first disease trigger and the disease symptom has a Cox Hazard Ratio greater than 1 and a p-value less than or equal to a threshold p-value.

5. The method of claim 1, further comprising:
receiving, by the client device from the server, a second indication of a strength of a statistical association between a second disease trigger and the disease symptom for the user; and displaying a second trigger icon corresponding to the second disease trigger within the trigger map, wherein the position of the second trigger icon within the trigger map is based on the received second indication of a statistical association strength between the second disease trigger and the disease symptom, and wherein a second trigger icon size is based on how much the user has been exposed to the second disease trigger within a defined timeframe corresponding to the second disease trigger.

6. The method of claim 5, further comprising:
receiving, by the client device from the server, a third indication of a statistical association strength between the disease symptom and a combination of the first and second disease triggers; and
displaying a combination icon corresponding to the first and second disease triggers within the trigger map, wherein a combination icon position within the trigger map is based on the received third indication of the statistical association strength between the disease symptom and the combination of the first and second disease triggers, and wherein a combination icon size is based on how much the user has been exposed to the first disease trigger within the defined timeframe corresponding to the first disease trigger and how much the user has been exposed to the second disease trigger within the defined timeframe corresponding to the second disease trigger.

7. The method of claim 5, further comprising:
receiving, by the client device from the server, a current likelihood that the user will experience the disease symptom within a future timeframe, wherein the likelihood is based at least in part on one or more of (i) the statistical association strength between the first disease trigger and the disease symptom, (ii) the statistical association strength between the second disease trigger and the disease symptom, (iii) the statistical association strength between the disease symptom and the combination of the first and second disease triggers; (iv) how much the user has been exposed to the first disease trigger within the defined timeframe corresponding to the first disease trigger, and/or (v) how much the user has been exposed to the second disease trigger within the defined timeframe corresponding to the second disease trigger;
displaying a risk meter for the disease symptom within the graphical user interface; and
displaying a risk indicator within the risk meter, wherein a risk indicator position within the risk meter is based on the value of the current likelihood that the user will experience the disease symptom within the future timeframe, and wherein a risk indicator size within the risk meter is based on a confidence level of the current likelihood that the user will experience the disease symptom within the future timeframe.

8. The method of claim 1, further comprising:
determining that an event relating to the first disease trigger has occurred;
in response to determining that the event relating to the first disease trigger has occurred, displaying a first disease prompt in the graphical user interface, wherein the first disease prompt comprises: (i) the first disease trigger icon, (ii) a request to enter one or more first disease trigger characterization metrics corresponding to the user's exposure to the first disease trigger, and (iii) an indication of acceptable values for each of the one or more requested first disease trigger characterization metrics;

receiving one or more of the requested one or more first disease trigger characterization metrics from the user via the graphical user interface; and transmitting the one or more received first disease trigger characterization metrics to the server.

9. The method of claim 8, further comprising:

receiving a fourth indication of a statistical association between the disease symptom and a combination of the first disease trigger and a third disease trigger; and at least partially in response to receiving the fourth indication of the statistical association between the disease symptom and the combination of the first and third disease triggers, displaying a second disease prompt in the graphical user interface, wherein the second disease prompt comprises: (i) a third disease trigger icon corresponding to the third disease trigger, (ii) a request to enter one or more third disease trigger characterization metrics corresponding to the user's exposure to the third disease trigger, and (iii) an indication of acceptable values for each of the one or more requested third disease trigger characterization metrics;

receiving one or more of the requested one or more third disease trigger characterization metrics from the use via the graphical user interface; and transmitting the one or more received third disease trigger characterization metrics to the server.

10. The method of claim 1, wherein the user is a member of a user population, and wherein the method further comprises:

receiving, from the server, disease trigger data for a plurality of users in the user population; and displaying a user population trigger map for the disease symptom within the graphical user interface, wherein the user population trigger map shows one or more relationships between (i) one or more disease triggers and (ii) one or more users of the user population.

11. The method of claim 1, wherein the user is a member of a user population, and wherein the method further comprises:

receiving, from the server, an identification of a trigger group comprising one or more other users in the population who have at least one disease trigger in common with the user;

in response to receiving the identification, displaying within the graphical user interface, an invitation to share disease trigger information with at least one user in the identified trigger group;

receiving, from the user, a selection of one or more users from the identified trigger group; and in response to receiving the selection from the user, transmitting to the server, a request to share disease trigger information with the selected users, wherein the request comprises at least one of (i) an anonymity level for sharing disease trigger information with selected users, (ii) an amount of disease trigger information to share with the selected users, and/or (iii) a type of disease trigger information to share with the selected users.

12. The method of claim 1, further comprising:

receiving, from the server, a message reminding the user to either (i) avoid a particular disease trigger or (ii) engage in a particular protector, wherein the disease trigger comprises at least one of an event, exposure, action, or conduct related to and/or performed by the user that has a potential to cause the user to experience the disease symptom, and wherein the protector comprises at least one of an event, exposure, action, or conduct related to and/or performed by the user that has a potential to prevent the user from experiencing the disease symptom; and in response to receiving the message, display the message within the graphical user interface.

13. A tangible, non-transitory computer readable media comprising instructions, wherein the instructions, when executed by one or more processors, cause the one or more processors to perform functions comprising:

providing, by way of the graphical user interface of the client device, a plurality of input prompts corresponding to a set of disease triggers that are determined to be relevant to a user of the client device experiencing a disease symptom;

receiving, by way of the graphical user interface of the client device, a plurality of inputs relating to the disease symptom and the set of disease triggers relevant to a user of the client device experiencing the disease symptom;

receiving, by the client device from a server based on the plurality of inputs, a first indication of a statistical association strength between a first disease trigger in the set of disease triggers and the disease symptom for the user of the client device, wherein the server is configured to use a processor to identify the set of disease triggers for the user and to track the plurality of inputs received by the client device to determine associations between the set of disease triggers and the disease symptom; and responsive to receiving the first indication of the strength of the statistical association between first disease trigger and the disease symptom, configuring the graphical user interface of the client device to indicate a risk of the user experiencing the disease, wherein indicating the risk of experiencing the disease symptom comprises displaying, by the client device, a trigger map for the disease symptom within the graphical user interface, wherein the trigger map includes trigger icons representing disease triggers associated with the disease symptom, and wherein displaying the trigger map within the graphical user interface comprises:

displaying, by way of the graphical user interface of the client device, a first trigger icon within the trigger map, wherein the first trigger icon corresponds to the first disease trigger, wherein the position of the first trigger icon within the trigger map is based on the received first indication of the statistical association strength between the first disease trigger and the disease symptom, and wherein a first trigger icon size is based on how much the user has been exposed to the first disease trigger within a defined timeframe corresponding to the first disease trigger, wherein the first trigger icon size and position within the graphical user interface indicates a risk of experiencing the disease symptom associated with (i) the statistical association strength between the first disease trigger and the disease symptom and (ii) how much the user has been exposed to the first disease trigger.

14. The computer readable media of claim 13, wherein the functions further comprise:

receiving, by the client device from the server, an indication of a statistical association strength between a protector and the disease symptom for the user, wherein the protector comprises at least one of an event, exposure, action, or conduct related to and/or performed by the user that can prevent the user from experiencing the disease symptom; and displaying a protector icon corresponding to the protector within the trigger map, wherein protector icon position within the trigger map is based on the received indication of the statistical association strength between the protector and the disease symptom, and wherein a protector icon size is based on how much the user has been exposed to the protector within a defined timeframe corresponding to the protector.

15. The computer readable media of claim 13, the functions further comprising:

receiving, by the client device from the server, a second indication of a strength of a statistical association between a second disease trigger and the disease symptom for the user; and displaying a second trigger icon corresponding to the second disease trigger within the trigger map, wherein the position of the second trigger icon within the trigger map is based on the received second indication of a statistical association strength between the second disease trigger and the disease symptom, and wherein a second trigger icon size is based on how much the user has been exposed to the second disease trigger within a defined timeframe corresponding to the second disease trigger.

16. The computer readable media of claim 15, the functions further comprising:

receiving, by the client device from the server, a third indication of a statistical association strength between the disease symptom and a combination of the first and second disease triggers; and displaying a combination icon corresponding to the first and second disease triggers within the trigger map, wherein a combination icon position within the trigger map is based on the received third indication of the statistical association strength between the disease symptom and the combination of the first and second disease triggers, and wherein a combination icon size is based on how much the user has been exposed to the first disease trigger within the defined timeframe corresponding to the first disease trigger and how much the user has been exposed to the second disease trigger within the defined timeframe corresponding to the second disease trigger.

17. The computer readable media of claim 15, the functions further comprising:

receiving, by the client device from the server, a current likelihood that the user will experience the disease symptom within a future timeframe, wherein the likelihood is based at least in part on one or more of (i) the statistical association strength between the first disease trigger and the disease symptom, (ii) the statistical association strength between the second disease trigger and the disease symptom, (iii) the strength of the statistical association strength between the disease symptom and the combination of the first and second disease triggers; (iv) how much the user has been exposed to the first disease trigger within the defined timeframe corresponding to the first disease trigger, and/or (v) how much the user has been exposed to the second disease trigger within the defined timeframe corresponding to the second disease trigger;

displaying a risk meter for the disease symptom within the graphical user interface; and displaying a risk indicator within the risk meter, wherein a risk indicator position within the risk meter is based on the value of the current likelihood that the user will experience the disease symptom within the future timeframe, and wherein a risk indicator size within the risk meter is based on a confidence level of the current likelihood that the user will experience the disease symptom within the future timeframe.

18. The computer readable media of claim 13, the functions further comprising:

determining that an event relating to the first disease trigger has occurred;

in response to determining that the event relating to the first disease trigger has occurred, displaying a first disease prompt in the graphical user interface, wherein the first disease prompt comprises: (i) the first disease trigger icon, (ii) a request to enter one or more first disease trigger characterization metrics corresponding to the user's exposure to the first disease trigger, and (iii) an indication of acceptable values for each of the one or more requested first disease trigger characterization metrics;

receiving one or more of the requested one or more first disease trigger characterization metrics from the user via the graphical user interface; and transmitting the one or more received first disease trigger characterization metrics to the server.

19. The computer readable media of claim 18, the functions further comprising:

receiving a fourth indication of a statistical association between the disease symptom and a combination of the first disease trigger and a third disease trigger; and at least partially in response to receiving the fourth indication of the statistical association between the disease symptom and the combination of the first and third disease triggers, displaying a second disease prompt in the graphical user interface, wherein the second disease prompt comprises: (i) a third disease trigger icon corresponding to the third disease trigger, (ii) a request to enter one or more third disease trigger characterization metrics corresponding to the user's exposure to the third disease trigger, and (iii) an indication of acceptable values for each of the one or more requested third disease trigger characterization metrics;

receiving one or more of the requested one or more third disease trigger characterization metrics from the user via the graphical user interface; and transmitting the one or more received third disease trigger characterization metrics to the server.

20. The computer readable media of claim 13, wherein the user is a member of a user population, and wherein the functions further comprise:

receiving, from the server, disease trigger data for a plurality of user in the user population; and displaying a user population trigger map for the disease symptom within the graphical user interface, wherein the user population trigger map shows one or more relationships between (i) one or more disease triggers and (ii) one or more users of the user population.

21. The computer readable media of claim 13, wherein the user is a member of a user population, and wherein the functions further comprise:

receiving, from the server, an identification of a trigger group comprising one or more other user in the population who have at least one disease trigger in common with the user;

in response to receiving the identification, displaying within the graphical user interface, an invitation to share disease trigger information with at least one user in the identified trigger group;

receiving, from the user, a selection of one or more users from the identified trigger group; and in response to receiving the selection from the user, transmitting to the server, a request to share disease trigger information with the selected users, wherein the request comprises at least one of (i) an anonymity level for sharing disease trigger information with selected users, (ii) an amount of disease trigger information to share with the selected users, and/or (iii) a type of disease trigger information to share with the selected users.

22. The computer readable media of claim 13, wherein the functions further comprise:

receiving, from the server, a message reminding the user to either (i) avoid a particular disease trigger or (ii) engage in a particular protector, wherein the disease trigger comprises at least one of an event, exposure, action, or conduct related to and/or performed by the user that has a potential to cause the user to experience the disease symptom, and wherein the protector comprises at least one of an event, exposure, action, or conduct related to and/or performed by the user that has a potential to prevent the patient from experiencing the disease symptom; and in response to receiving the message from the server, display the message within the graphical user interface.

23. The method of claim 1, further comprising:

providing, by way of the graphical user interface of the client device, an instruction for an action related to the first disease trigger for reducing the risk of the user experiencing the disease symptom.

24. The method of claim 1, wherein providing the plurality of input prompts corresponding to the set of disease triggers that are determined to be relevant to a user of the client device experiencing a disease symptom comprises, for at least one disease trigger in the set of disease triggers:

detecting, using one or more sensors of the client device, that an event has occurred that is associated with a disease trigger of the disease symptom; and responsive to detecting that the user has completed the action associated with the disease trigger, prompting the user to provide inputs related to the disease trigger.

25. The method of claim 1, wherein providing the plurality of input prompts corresponding to the set of disease triggers relevant to a user of the client device experiencing a disease symptom comprises:

determining relevant disease factors from a plurality of disease triggers associated with a disease symptom, wherein the relevant disease factors comprise a subset of the plurality of disease triggers that are known or suspected to be associated with the user experiencing the disease symptom; and reducing the input prompts based on only providing input prompts related to the relevant disease factors.

26. The method of claim 1, further comprising:

displaying, by way of the graphical user interface of the client device, a third trigger icon within the trigger map, wherein the third trigger icon corresponds to a disease factor of the disease symptom, and wherein the first trigger icon and the third trigger icon are positioned differentially within the graphical user interface based on the first trigger icon being associated with a disease trigger and the third trigger icon being associated with a disease factor.

* * * * *